(12) United States Patent
Hancock et al.

(10) Patent No.: US 11,337,755 B2
(45) Date of Patent: May 24, 2022

(54) SKIN TREATMENT APPARATUS

(71) Applicant: BANGOR UNIVERSITY, Gwynedd (GB)

(72) Inventors: Christopher Paul Hancock, Bath and North East Somerset (GB); Paul Horwitz, Buckinghamshire (GB); George Ullrich, Gwynedd (GB); David Webb, Gwynedd (GB)

(73) Assignee: BANGOR UNIVERSITY, Gwynedd (GB)

( * ) Notice: Subject to any disclaimer, the term of this patent is extended or adjusted under 35 U.S.C. 154(b) by 715 days.

(21) Appl. No.: 16/302,072

(22) PCT Filed: May 24, 2017

(86) PCT No.: PCT/EP2017/062542
§ 371 (c)(1),
(2) Date: Nov. 15, 2018

(87) PCT Pub. No.: WO2017/202911
PCT Pub. Date: Nov. 30, 2017

(65) Prior Publication Data
US 2019/0216541 A1    Jul. 18, 2019

(30) Foreign Application Priority Data
May 24, 2016 (GB) ..................... 1609110

(51) Int. Cl.
*A61B 18/18* (2006.01)
*A61B 17/00* (2006.01)
*A61B 18/00* (2006.01)

(52) U.S. Cl.
CPC ............... *A61B 18/1815* (2013.01); *A61B 2017/00101* (2013.01); *A61B 2017/00747* (2013.01);
(Continued)

(58) Field of Classification Search
CPC ...... A61B 18/1815; A61B 2017/00101; A61B 2017/00747; A61B 2018/0047;
(Continued)

(56) References Cited

U.S. PATENT DOCUMENTS 4,108,147 A    8/1978  Kantor
5,571,154 A   11/1996  Ren
(Continued)

FOREIGN PATENT DOCUMENTS

WO   WO 2008/068485 A2   6/2008
WO   WO 2009/075879 A8   6/2009

OTHER PUBLICATIONS

International Search Report and Written Opinion of related International Applicaiton No. PCT/EP2017/062542 dated Aug. 24, 2017.
(Continued)

*Primary Examiner* — Michael F Peffley
(74) *Attorney, Agent, or Firm* — ArentFox Schiff LLP

(57) ABSTRACT

Skin treatment apparatus comprising an energy applicator structure configured to establish heating or ablation at a predetermined and controllable (i.e. selectable) depth below a surface of skin tissue with which it is in contact. The applicator structure may receive a cooling medium and microwave frequency electromagnetic energy, which provide a combined treatment effect that results in heating or ablation in a zone beneath the skin surface. The applicator may be a waveguide (e.g. waveguide horn antenna) with internal shielding configured to provide a substantially uniform heating effect. The applicator may include a thermal camera to monitor treatment.

20 Claims, 17 Drawing Sheets

(52) U.S. Cl.
CPC ............... *A61B 2018/00017* (2013.01); *A61B 2018/00029* (2013.01); *A61B 2018/00035* (2013.01); *A61B 2018/0047* (2013.01); *A61B 2018/00047* (2013.01); *A61B 2018/00476* (2013.01); *A61B 2018/00577* (2013.01); *A61B 2018/00642* (2013.01); *A61B 2018/00678* (2013.01); *A61B 2018/00702* (2013.01); *A61B 2018/00708* (2013.01); *A61B 2018/00714* (2013.01); *A61B 2018/00785* (2013.01); *A61B 2018/00809* (2013.01)

(58) Field of Classification Search
CPC ........... A61B 2018/00017; A61B 2018/00029; A61B 2018/00035; A61B 2018/00047; A61B 2018/00476; A61B 2018/00577; A61B 2018/00642; A61B 2018/00678; A61B 2018/00702; A61B 2018/00708; A61B 2018/00714; A61B 2018/00785; A61B 2018/00809

See application file for complete search history.

(56) References Cited

U.S. PATENT DOCUMENTS

| | | | |
|---|---|---|---|
| 6,463,336 | B1 | 10/2002 | Mawhinney |
| 9,427,285 | B2* | 8/2016 | Deem ................ A61N 5/02 |
| 2008/0269851 | A1* | 10/2008 | Deem ................ A61N 5/02 |
| | | | 607/101 |
| 2010/0036369 | A1 | 2/2010 | Hancock |
| 2010/0114086 | A1* | 5/2010 | Deem ................ A61N 5/02 |
| | | | 606/33 |
| 2013/0035680 | A1* | 2/2013 | Ben-Haim ............ A61N 5/04 |
| | | | 606/33 |
| 2014/0303608 | A1* | 10/2014 | Taghizadeh ........... A61B 18/14 |
| | | | 606/20 |
| 2014/0378959 | A1* | 12/2014 | Spertell ............. A61B 18/1815 |
| | | | 606/33 |

OTHER PUBLICATIONS

Search Report in United Kingdom Application No. GB 1609110.0 dated Nov. 25, 2016.

* cited by examiner

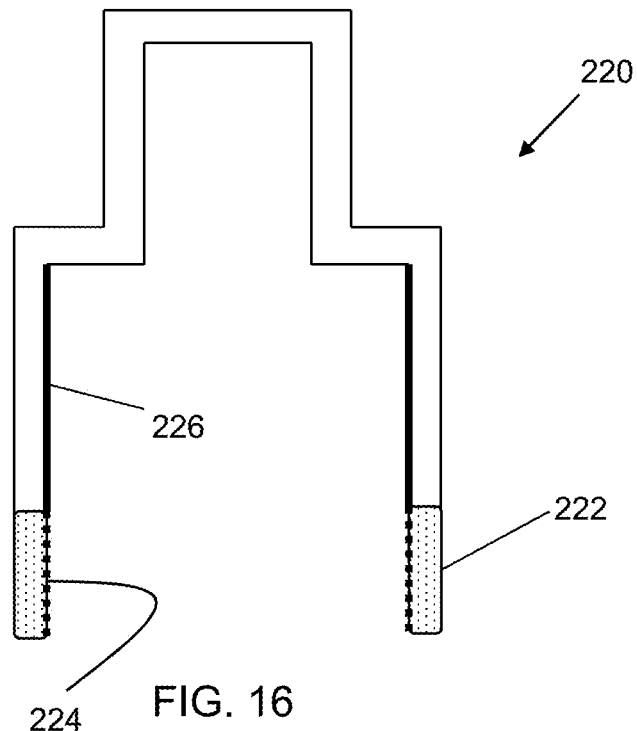
FIG. 16
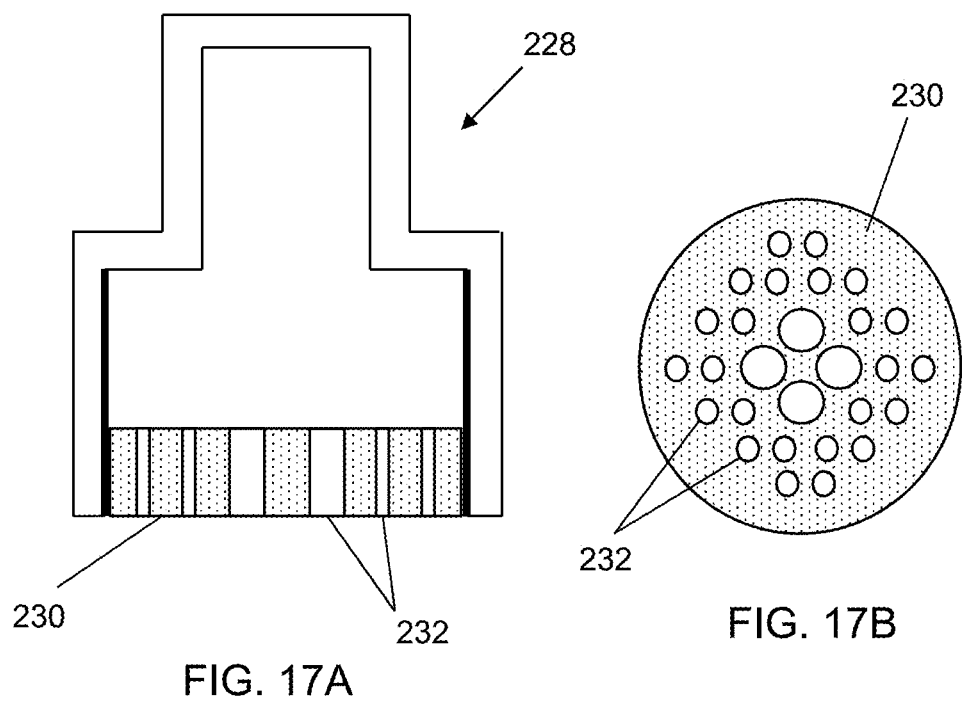
FIG. 17A
FIG. 17B

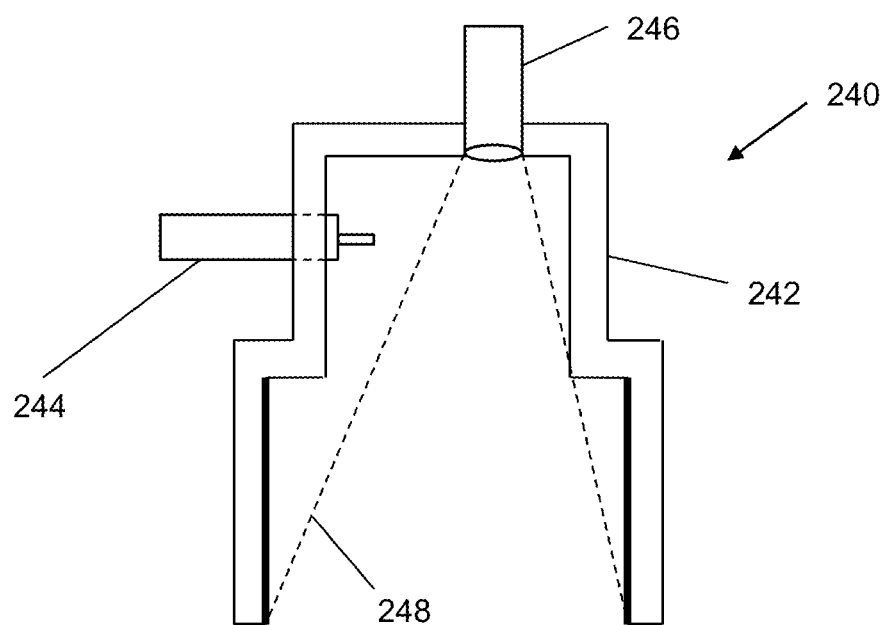
FIG. 18
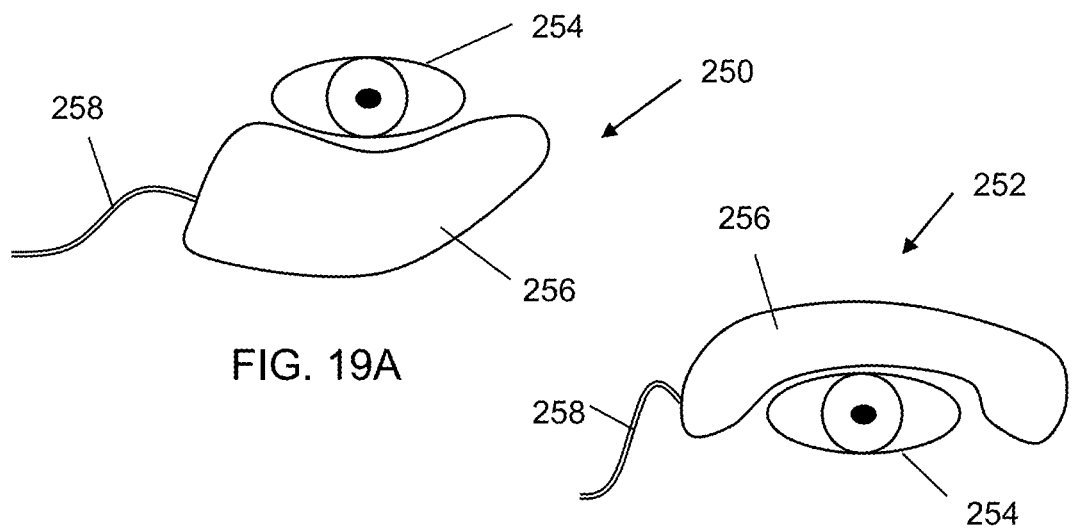
FIG. 19A
FIG. 19B

SKIN TREATMENT APPARATUS

CROSS-REFERENCED TO RELATED APPLICATIONS

This application is a National Stage entry of International Application No. PCT/EP2017/062542, filed on May 24, 2017, which claims priority to European Patent Application No. 1609110.0, filed on May 24, 2016. The disclosures of the priority applications are incorporated in their entirety herein by reference.

TECHNICAL FIELD

The present invention relates to a skin treatment apparatus and methods for medical or cosmetic treatment of skin tissue through heating or ablation by the application of heat to skin tissue. In particular the invention pertains to targeted heating below the surface of skin tissue. The invention may be used for treatment of benign and malignant skin tumours, dermatitis, hair removal or wrinkle reduction.

BACKGROUND OF THE INVENTION

There are various types of skin treatment systems that use ablation or heating of the skin to treat skin disease or to rejuvenate the skin. Skin treatment is a growing market, and there is a consumer-led desire for non-invasive treatments for disease and skin rejuvenation.

The skin is the largest organ of the human body and is made up of different layers each of which have a different composition which causes a different reaction to heating in each layer.

Ablation prompts a number of responses from skin tissue. For example, ablation of a region of skin tissue can stop that region from functioning and may stimulate healing in the skin as the ablated region is treated as a wound by the skin. Ablation may be used in the treatment of skin cancer, lesions or tumours. Treatment of skin tissue with sufficient heating can stimulate sub-surface changes in the skin by denaturing proteins causing a healing response from the skin tissue. It is known that the use of heat beneath the surface of the skin, even without causing ablation, can stimulate new skin growth and collagen growth which will cause skin to look more youthful, cause the skin to tighten and reduce the severity of wrinkles.

It is known to use controlled radio frequency (RF) electromagnetic radiation, e.g. with a frequency between 10 kHz and 300 MHz, and/or infrared or near infrared laser light to cause heating in skin tissue. Skin appears as a dielectric medium to RF radiation. When RF radiation passes through the skin, heat is generated at and beneath the surface of the skin tissue. The laser light heats skin tissue by absorption of the laser light as it passes into the skin.

In combination with the application of low frequency RF electromagnetic radiation and/or laser light, it is also known to cool the surface of the skin to reduce the risk of damage or burning at the surface due to excessive heating. Cooling can, for example, be achieved through the use of cryogenic sprays or thermo-electric cooling using Freon, tetrafluoroethane or other such refrigerants.

There are a number of drawbacks of using RF electromagnetic radiation. RF electromagnetic waves penetrate deep into the skin, which means it can be difficult to predict and control the depth to which heating occurs. Moreover, the dielectric heating induced by low frequency RF radiation causes the heat to be spread by conduction through the skin tissue. Heat transfer by conduction can lead to uneven heating, and when cooling is applied to the skin it counteracts and disrupts the conduction of heat to cause a reduced heating effect or to eliminate any heating.

Laser light is absorbed only in a small region of skin tissue where the laser light is incident. This causes significant heating in those regions generating hotspots from which heat is then transferred to the surrounding skin tissue by conduction. The hotspots can cause uneven heating and the overall heating is affected in the same way by cooling as RF radiation. The depth of penetration of laser light and therefore the heating effect depends on skin composition at the location where the laser light is applied and is therefore unpredictable. This can lead to variation in results between different parts of the body and different patients.

SUMMARY OF THE INVENTION

At its most general, the present invention provides a treatment apparatus for skin in which an applicator structure for contacting a region of skin is configured to establish heating or ablation at a predetermined and preferably controllable (i.e. selectable) depth below the surface of the skin tissue. For example, the applicator structure may be arranged to receive a cooling medium and microwave frequency electromagnetic energy, which provide a combined treatment effect that results in heating or ablation in a zone beneath the skin surface. The applicator may be configured to provide a substantially uniform heating effect.

The invention can be used for treating skin tissue below the surface of the skin. Such treatment may be applicable to various stages of skin cancer, dermatitis, hair removal or collagen shrinkage.

According to the invention, there may be provided a skin treatment apparatus comprising: a microwave source for generating microwave electromagnetic energy; an applicator for mounting over a region of skin, the applicator comprising: an energy delivery structure for conveying the microwave electromagnetic energy; and a microwave feed structure coupled between the microwave source and waveguide for launching the microwave electromagnetic energy into the energy delivery structure, wherein the apparatus is controllable to deliver the microwave electromagnetic energy in a manner that induces a thermal profile in the region of skin, the thermal profile having a maximum temperature that occurs at a predetermined distance beneath a surface of the region of skin.

In a simplified form, the skin is composed of three layers. The top layer is called the epidermis, the middle layer is the dermis and the bottom layer is the subcutaneous layer. Using the present invention it may be possible to controllably target energy into the dermis without causing unwanted heating elsewhere. The dermis contains many of the structural features which dictate the properties of skin such as protein fibres, e.g. collagen. Hair follicles and sweat glands are also located in the dermis. As such, for treating skin tumours which have spread to the dermis and for collagen shrinkage and hair removal it is highly desirable to penetrate heat into the dermis. When heat is applied to the dermis it is desirable to protect the epidermis from damage caused by the heat. One advantage of the microwave frequency electromagnetic energy of the present invention is the ability of to deliver heat instantaneously. Alone or in conjunction with a cooling medium, the applicator may be capable of producing controlled, predictable and uniform heating or ablation in the dermis.

The energy delivery structure may be any structure suitable for mounting on or over a region of skin in order to convey, e.g. permit propagation of, microwave energy into skin tissue. In one example, the energy delivery structure is a waveguide. The waveguide may be rectangular or cylindrical or any other shape suitable for treating a region of skin tissue.

Waveguides for electromagnetic energy may have Transverse Electric (TE) or Transverse Magnetic (TM) modes. The fundamental mode of a rectangular waveguide (a waveguide with a rectangular cross-section in a plane perpendicular to the length of the waveguide) or a circular waveguide is a TE mode. The fundamental mode of a rectangular waveguide is the TE10 mode, and the fundamental mode of a circular waveguide is the TE11 mode. Other shapes of waveguide, for example a hexagonal or square waveguide, may have different fundamental modes. The invention may use a rectangular waveguide, but is not necessarily limited to this configuration. To aid use of the treatment apparatus, the applicator may be hand-held. The applicator may also be moulded to form a complementary fit for a hand. The waveguide may have a transformer section to change the impedance of the microwave frequency electromagnetic energy. The change in impedance may be necessary to change the impedance from a value of the microwave feed structure to a value closer to the impedance of skin tissue. The transformer section may be a single step change in the dimensions of the interior of the waveguide, a multi-step change, a funnel shaped taper to change the dimensions of the interior of the waveguide without a step change or a suitable transformer shape for changing the impedance of the waveguide along the length of the waveguide.

The electromagnetic field emitted from the aperture of the waveguide may have an intensity profile which has a maximum at the centre of the aperture and is at a minimum at the edges of the aperture. If the aperture is rectangular, the intensity profile of the electromagnetic filed may be a cosine distribution along the long axis of the aperture. The distribution of the field along the short axis of the aperture may be steep in a boundary region at the edges of the short axis close to the walls at the open end of the waveguide defining the aperture, and may be a shallow dome between the boundary regions. This distribution along the short axis may be present along the length of the distribution along the long axis of the aperture. For a rectangular aperture, an ideal intensity profile may be equal across the area of the aperture.

The waveguide may comprise a microwave shield on an interior wall adjacent the treatment aperture, the microwave shield covering or occupying part or parts (preferably opposing parts) of the interior wall. The purpose of the microwave shield is to flatten the energy profile. The shield may be made from any one or more of: a dielectric material (e.g. a material having a higher relative permittivity than the interior of the cavity, and preferably exhibiting low loss at the frequency of the microwave energy); a perfect magnetic conductor (PMC); a ferrite material; and a metamaterial.

The dielectric material may be PTFE, PEEK or ceramic. The material may have a thickness equal to or greater than 4 mm, e.g. in a range from 4 to 6 mm, preferably 5 mm. The PMC material results in zero magnetic field along its surface. Any suitable artificial magnetic conductor surface may be used for this purpose, e.g. a lattice that does not conduct AC currents in a particular frequency band, or a frequency selective surfaces (FSS) based on slot or printed dipoles on a dielectric slab (e.g. arrays of elements having a square or cross or spiral shape). A ferrite material can be used to achieve a similar effect by applying an external magnetic field to tune its electric field profile.

For example, the microwave shield my comprise a coating on the surface on the interior wall or an insert placed inside the waveguide to block the section of the interior from interacting with the microwave frequency electromagnetic energy and itself interact with the microwave frequency electromagnetic energy.

By metamaterial it is meant a material which has a negative refractive index and/or a material which has a negative permittivity. In one example, the microwave shield comprises a pair of blocks mounted on opposing inner surfaces of the cavity and having a plurality of parallel, spaced apart, conductive strips extending in a direction toward the aperture.

The microwave shield can be arranged to shape the emitted microwave electromagnetic energy as a uniform electromagnetic field across the treatment aperture. For example, the microwave shield may be made from dielectric material or metamaterial arranged to create a quasi perfect magnetic conductor boundary condition at two opposing sides of the aperture. The waveguide can be dimensioned to carry the microwave frequency electromagnetic energy in a fundamental mode, which interacts with the boundary condition set up by the microwave shield such that the electromagnetic field emitted by the waveguide is in a quasi-TEM mode.

The edges of the microwave shields that face out of the aperture may be covered by a grounded conductive material, e.g. foil or the like. This material acts as a reflector to prevent heating directly in front of the microwave shields where the E field intensity decreases with proximity to the side of the cavity.

The applicator may be arranged to fit against or around a particular anatomical feature on a patient's body. For example, the applicator may be shaped to fit above or beneath a patient's eye or mouth. To improve fit and facilitate uniform delivery of energy, the applicator may comprise a deformable contact portion for abutting the region of skin.

In one example, the waveguide may comprise a flexible substrate having a microwave emitting structure fabricated thereon. The microwave emitting structure may be a slotted microstrip antenna.

In another example, the waveguide may comprise a waveguide body that defines a waveguide cavity having an interior electrically conductive surface dimensioned to support propagation of the microwave electromagnetic energy. The waveguide cavity may comprise a treatment aperture (e.g. as discussed above) for locating over the region of skin, the treatment aperture being dimensioned to emit the microwave electromagnetic energy as an electromagnetic field. The deformable contact portion may comprise a deformable rim one the waveguide body around the aperture. The deformable rim may be made from any suitable biocompatible material, e.g. silicone rubber or the like. The deformable rim may detachable from the waveguide body, e.g. to allow it to be sterilised and re-used or disposed of easily. The deformable rim may have a metallised inner surface that is electrically connected to the interior electrically conductive surface of the waveguide cavity. This can ensure that the propagation of microwave energy to the region of skin is not affected by the presence of the deformable contact portion.

The waveguide may be loaded as a means of controlling the shape or configuration of the microwave energy that is delivered into the region of skin. For example, the applicator may comprise a loading unit mountable on the waveguide to load the waveguide. In one example, the loading unit may be arranged to shape the microwave electromagnetic into a fractionated electromagnetic field, i.e. to transform the uniform field into a plurality of discrete energy delivery points arranged in an array over the region of skin. Compared with a uniform delivery of energy at the tip of an applicator, fractional energy is delivered in columnar patterns, which forms dots on the skin surface, leaving untreated tissue in between the delivered energy. The loading unit may be can be configured to set a pattern density and shape, whereby the energy delivered per dot and size or width of each dot, can be controlled, e.g. dependent upon the skin condition and severity of the condition being treated.

If the waveguide comprises a waveguide body that defines a waveguide cavity having an interior electrically conductive surface dimensioned to support propagation of the microwave electromagnetic energy, the loading unit may be arranged as a cover mountable in or over the treatment aperture. The cover may have a shape that matches the shape of the aperture. It may be mounted in the aperture by an interference fit or the like.

The cover need not act as a loading unit, i.e. it may be transparent to the microwave energy. In this example, it may act simply as a container for cooling medium present in the waveguide. The cover may stop skin tissue from entering the waveguide through the aperture, which could alter the microwave frequency electromagnetic energy distribution inside the waveguide and/or the field distribution emitted into the skin from the aperture. Having a perforation in the cover may allow the cooling medium to contact the surface of the skin tissue directly. The cover may have a plurality of perforations to allow the cooling medium to be applied to the skin in multiple locations across the aperture.

The power generated by the microwave source may be controllable. The microwave source may include a monitoring system configured to detect the power delivered to the waveguide by the microwave source, and the power generated by the microwave source may be controlled on the basis of the delivered power detected by the monitoring system. The monitoring system may be further configured to detect the power reflected back to the microwave source so the power delivered to the waveguide may be further controlled on the basis of the reflected power detected by the monitoring system. This arrangement provides the ability to compensate for varying power output by the microwave source, and for varying impedances in the skin tissue to be treated, for example due to moisture, tissue structure or other aspects, to control finely the level of energy emitted into the skin tissue and to focus the emitted field as a further means of control. The monitoring system may also include a monitoring unit, the monitoring unit being a part of a control system which may be used to control the apparatus.

For example, the applicator may comprise an imaging device arranged to capture an image of the region of skin during treatment. The imaging device may obtain visual images of the region of skin, e.g. to assist in locating the applicator. Alternatively or additionally, the imaging device may be arranged to detect infrared radiation. This can give information indicative of the temperature of the skin surface. As such, the imaging device may be arranged to generate an output indicative of temperature at the surface of the region of skin, and wherein the microwave source is controllable based on the output from the imaging device, e.g. using the monitoring system discussed above.

In this specification, the term "microwave" is used generally to denote a frequency range from 1 GHz to 300 GHz or more. It may include high frequencies that can be said to reside in the mm wave region. Preferably, the microwave source may be configured to generate a continuous wave microwave frequency electromagnetic signal. The microwave source may generate microwave frequency electromagnetic energy at a frequency equal to or greater than 10 GHz, e.g. 14.5 GHz, 24 GHz, 31 GHz, 45 GHz, 60 GHz, 77 GHz or 94 GHz.

The microwave feed structure may include a coaxial cable between the microwave source and the waveguide. The coaxial cable may terminate at a coupling section in the waveguide for launching the microwave frequency electromagnetic energy into the waveguide. The coupling section may comprise an E-field or The invention may also provide a method of treating skin tissue with microwave frequency electromagnetic energy, the method comprising: positioning an applicator over a region of skin, the applicator comprising: a waveguide for conveying the microwave electromagnetic energy; and a microwave feed structure coupled between the microwave source and waveguide; launching microwave electromagnetic energy into the waveguide; and controlling delivery of the microwave electromagnetic energy in a manner that induces a thermal profile in the region of skin, the thermal profile having a maximum temperature that occurs at a predetermined distance beneath a surface of the region of skin.

In one example, the invention may apply, in a single treatment operation, counteractive heating and cooling. The heating and cooling work together to define a heating profile that penetrates into the dermis without negatively affecting the epidermis. The apparatus may comprise a cooling medium, wherein the cooling medium is arranged to induce a negative thermal gradient through the region of skin, and wherein the delivered microwave electromagnetic element is arranged to induce a positive thermal gradient through the region of skin, and wherein the apparatus is arranged to balance the negative thermal gradient and positive thermal gradient to induce the thermal profile. The cooling medium may be an integral part of the applicator, e.g. so that the negative thermal gradient is applied in the same operation as the positive thermal gradient. However, this may be not be necessary. For example, the cooling medium may be applied in advance, e.g. as a cooling gel or other suitable heat sink, in order to create a preliminary thermal bias in the region of skin before the microwave energy is applied.

In one embodiment, the waveguide may comprise a treatment aperture for locating over the region of skin, the treatment aperture being dimensioned to emit the microwave electromagnetic energy as an electromagnetic field. The cooling medium may be delivered to or through the aperture. For example, the apparatus may include a cooling system configured to deliver a cooling medium through the waveguide to the aperture. The cooling medium may directly contact the region of skin, or, as discussed below, the aperture may be covered, in which case the cooling medium may thermally interact indirectly with the region of skin via a cover.

The cooling system may be include a circulation system for refreshing the cooling medium. This may be particular useful where the cooling medium is a liquid or gas. In one example, a passage for removing the cooling medium from a zone adjacent the aperture may be integrally formed in the walls of the aperture. One or more outlets for providing communication between the passage and the interior of the waveguide may be provided. The outlets may have a conductive mesh formed over them to prevent leakage of microwave energy.

The cooling system may operate to feed a cooling medium, which may be a liquid or a gas coolant, to the waveguide of the applicator. The cooling medium may be applied to the surface of the skin tissue to be treated or may be used to cool a section of the applicator which is in contact with a treatment region of the skin tissue. To apply the cooling medium to the surface of the skin tissue, the cooling medium may be introduced into the waveguide by a nozzle, spray, hose or other suitable means to pass the cooling medium through the waveguide to the aperture to the skin tissue. The cooling medium to be sent to the applicator may be stored or held in a reservoir or container, or alternatively may be supplied to the apparatus from an external supply. The cooling medium may be transferred to the applicator by a pump suitable for moving the coolant from the reservoir or external supply. The supply of cooling medium may be controlled and/or coordinated by a cooling system which may alter the flow-rate and/or the amount of coolant passed to the applicator.

Cooling can, for example, be achieved through the use of cryogenic sprays or thermo-electric cooling using Freon, tetrafluoroethane or other such refrigerants.

In other examples, the cooling medium may not pass through the waveguide. For example, the cooling medium can be a spray or cream that is applied to the region to be treated before the waveguide applicator. Alternatively, the cooling medium may be a heat sink (e.g. comprising a block of metal such as brass) or other mechanism for drawing thermal energy away from the skin surface (e.g. a Peltier cooler or the like), mounted on the waveguide applicator, e.g. on or adjacent the mouth of the waveguide itself.

Where the cooling medium comprises a material between the aperture of the waveguide and the skin, the properties of the material may be selected to improve an impedance match between the two surfaces, i.e. reduce the level of power being reflected back into the generator. Thus, if the material is a liquid, cream, or solid dielectric, the dielectric constant and thickness of the material may be selected to improve the impedance match.

The cooling medium may be delivered according to a first delivery schedule which, in the absence of other heating or cooling effects, is arranged to establish a temperature profile having a negative gradient towards the surface of the treatment region of skin tissue. The microwave frequency electromagnetic energy may be delivered through the aperture of the waveguide according to a second delivery schedule, which, in the absence of other heating or cooling effect is arranged to establish a temperature profile having a positive gradient towards the surface of the treatment region of skin tissue. The first and second delivery schedule can be coordinated to cause the temperature gradients to cooperate (e.g. superimpose) to form an ablation or heating zone at a predetermined depth below the surface of the treatment region of skin tissue. The predetermined depth may be from around 0.2 mm to 5 mm or more, depending on the location on the patient's body and the size of the region to be treatment. This is because lesions may have different depths and because the dermis may be a different depths art different areas on the body.

The cooling medium may be delivered in a series of pulses. The pulses of cooling medium may be synchronised with respective pulses or similar of microwave frequency electromagnetic energy to generate a combined heating regime. For example, the pulses of cooling medium may be modulated by controlling the flow rate of the coolant. The microwave frequency electromagnetic energy may be modulated by controlling its the amplitude. This may be done, for example by using a microprocessor and control algorithms in the control system or by being set on the control system by a user before delivery of the cooling medium or microwave frequency electromagnetic energy begins. The control system may have control algorithms, software algorithms and/or waveforms for monitoring, adjusting and/or controlling the signal generator and the cooling system.

Preferably, the method of the invention may be enacted using the skin treatment apparatus of the invention. According to the method of the invention, the aperture of the waveguide may have a cover, and when the aperture is positioned over the treatment region of skin tissue the cover may be in contact with the surface of the treatment region of skin tissue.

Preferably, when the cooling medium is delivered, the cooling medium may be delivered onto the treatment region of skin tissue.

In order to shrink collagen the skin treatment apparatus preferably must be capable of producing heat between 40° C. and 60° C. at a depth beneath the surface of the skin tissue. In an embodiment, the heating profile provided by the device may be controllable (e.g. selectable) to target a primary heating effect (i.e. a region or layer at which maximum heating occurs) at a selectable depth below the surface. The selectable depth may be in the range of 0.2 mm to 5 mm beneath the skin surface.

The use of microwave frequency electromagnetic energy addresses problems posed by the use of laser light and/or low frequency RF electromagnetic radiation in heating skin tissue. Due to the wavelength of microwave frequency electromagnetic waves the skin effect causes the microwaves to be absorbed by the skin tissue causing controllable heating of the skin tissue over a predictable and repeatable distance and distribution. The depth of penetration allows for evenly distributed heating over a large area and to a calculable depth. Because heat is generated in the skin tissue by absorption of the microwave frequency electromagnetic energy heat is produced quicker than with low frequency RF radiation. The quicker heating effect caused by microwave frequency electromagnetic energy than the use of low frequency RF radiation may also improve the healing process.

BRIEF DESCRIPTION OF THE DRAWINGS

For a better understanding of the invention, and to show how embodiments of the same may be carried into effect, reference will now be made, by way of example, to the accompanying drawings, in which:

FIG. 16 shows a cross-sectional view of a waveguide applicator that is another embodiment of the invention;

FIG. 17A shows a cross-sectional view of a waveguide applicator that is another embodiment of the invention;

FIG. 17B shows a top view of a detachable loading insert for use with the waveguide applicator shown in FIG. 17A;

FIG. 18 shows a cross-sectional view of a waveguide applicator that is another embodiment of the invention;

FIGS. 19A and 19B show schematic drawings of shaped flexible waveguide applicators that are embodiments of the invention;

DETAILED DESCRIPTION; FURTHER OPTIONS AND PREFERENCES

An embodiment of the invention comprises a skin treatment apparatus that has a waveguide with an aperture for emitting microwave frequency electromagnetic energy as an electromagnetic field when microwave frequency energy is generated by a microwave source connected to the waveguide. A cooling system is also connected to the waveguide to supply a cooling medium to the waveguide to provide cooling through the aperture.

When cooling is applied to skin tissue (e.g. by delivering a liquid coolant in a series of spray pulses), a temperature profile is established in the skin tissue through conduction. If a predetermined regime of pulses is set up a specific temperature profile can be produced and monitored. The cooling temperature profile has a negative gradient towards the surface of the skin tissue. By negative gradient towards the surface it is meant that the surface is coolest and the temperature increases as the distance from the surface of the skin increases, i.e. as the depth increases the temperature increases. When skin tissue is irradiated with the microwave frequency electromagnetic energy a temperature profile is established in the skin tissue. This heating temperature profile has a positive gradient towards the surface of the skin tissue, i.e. as the depth increases the temperature decreases. The heating profile is established due to absorption of the microwaves. The skin effect dictates the absorption profile in a material, in this case skin tissue, as the distance into the material increases. The cooling regime and the power of the microwave frequency electromagnetic energy can be manipulated to change the heating profiles. The two heating profiles cooperate to produce an ablation or heating zone at a depth below the surface of the skin tissue. In a band from the surface of the skin tissue to a depth below the surface, the cooling counteracts the heating caused in the band by the microwave frequency electromagnetic energy up to the region of heating.

In the ablation or heating zone any cooling effect caused by conduction or any other means is not sufficient to counteract the heating. This causes ablation in the skin tissue or heating to a level capable of denaturing proteins.

Below the ablation or heating zone, at a greater depth within the skin tissue than the ablation or heating zone, the microwave frequency electromagnetic energy is sufficiently dissipated due to the skin effect so as not to produce heating that is capable of causing damage to the skin tissue or of denaturing proteins.

Figure 1:
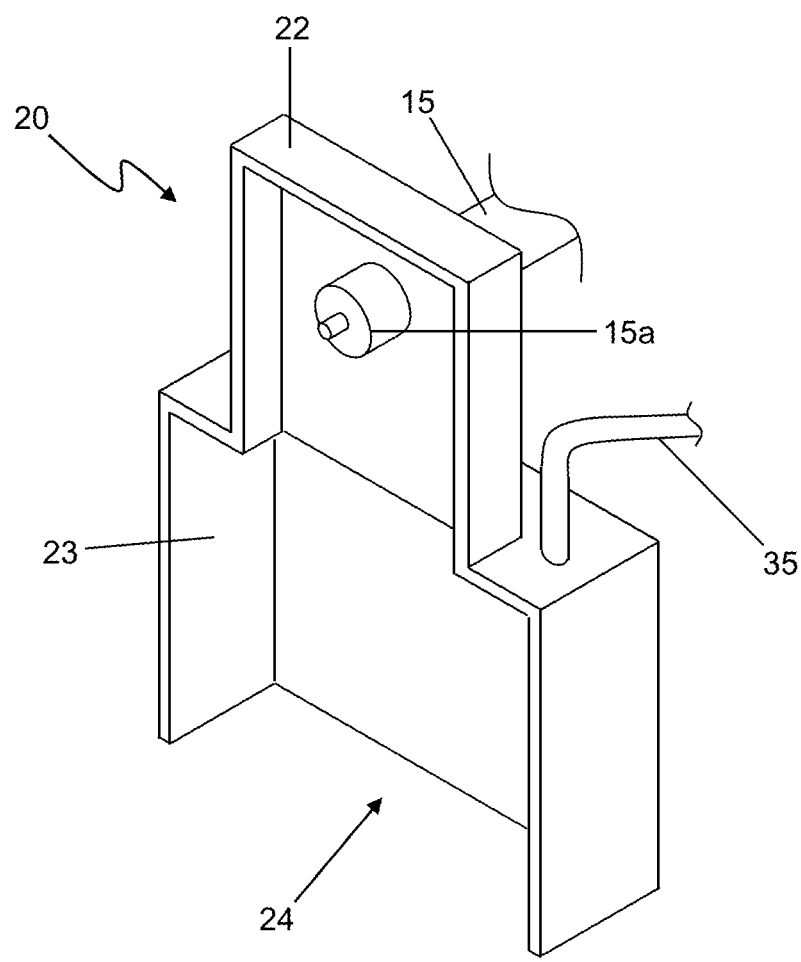
FIG. 1 shows a perspective view of a cross-section of the waveguide according to the invention.

FIG. 1 shows a cross-section of the applicator 20 of the skin treatment apparatus. The applicator comprises a waveguide 20a which has an open end that forms an aperture 24 and a closed end 22. The inside surface of the waveguide forms the interior walls 23 of the waveguide. The waveguide is connected to a microwave feed structure 15 which launches microwave frequency electromagnetic energy into the waveguide from a coupler 15a (e.g. E-field or H-field probe) at the end of the feed structure which is connected into the waveguide. The microwave frequency electromagnetic energy is generated by a microwave source 10 (not shown in FIG. 1). The applicator also has a cooling feed structure 35 for supplying a cooling medium into the waveguide through a nozzle or spray.

Figure 13:
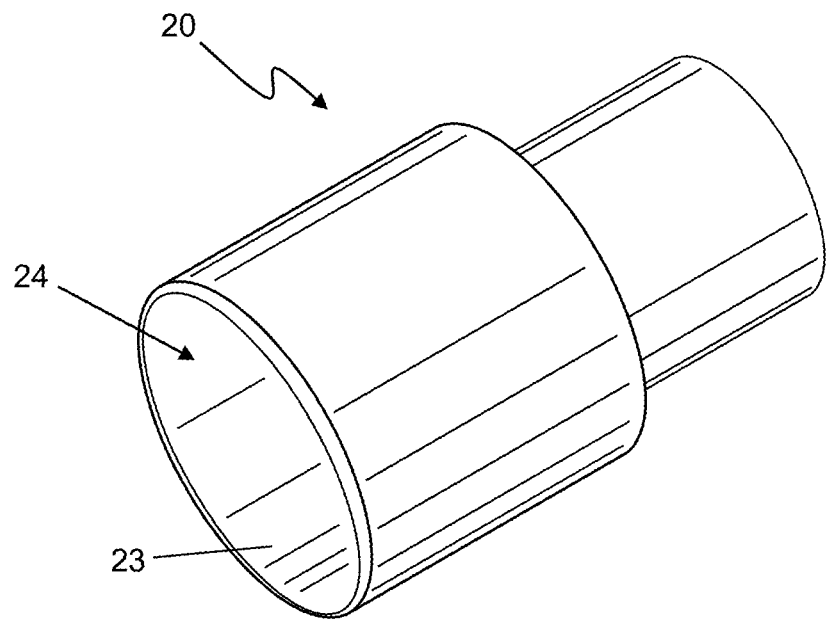
FIG. 13 shows a perspective view of another embodiment of the invention of a circular waveguide on its side.

The waveguide 20a shown in FIG. 1 is rectangular, i.e. has a rectangular cross-section in a plane perpendicular to the length (the dimension of the waveguide between the closed end of the waveguide and the aperture) of the waveguide. The waveguide may be square, circular (as shown in FIG. 13) or any other shape capable of supporting the propagation of electromagnetic energy.

In the embodiment shown in FIG. 1, the width (the long axis) and the height (the short axis) of the rectangular cross-section of the waveguide change down the length of the waveguide. The height and width of the rectangular cross-section at a point along the length of the waveguide affect the impedance and dictate the cut-off frequencies of the modes, including the fundamental mode, capable of being generated in the waveguide and at the aperture 24 of the wave guide. The change in the width and height of the rectangular cross-section forms a single step transformer section which changes the impedance of the waveguide from the impedance of the section near the closed end 22 of the waveguide, dimensioned to match the impedance of the microwave feed structure 15, to an impedance of skin tissue at the end of the waveguide with the aperture.

The step change in the height and width of the rectangular cross-section for the transformer section of the waveguide is at the same point along the length of the waveguide to minimise the number of locations and the amount of reflection of microwave frequency electromagnetic energy. This is shown in FIGS. 1 to 5. Each step change in a waveguide causes reflection of the energy propagating through the waveguide with more energy being reflected with a larger step.

Figure 3:
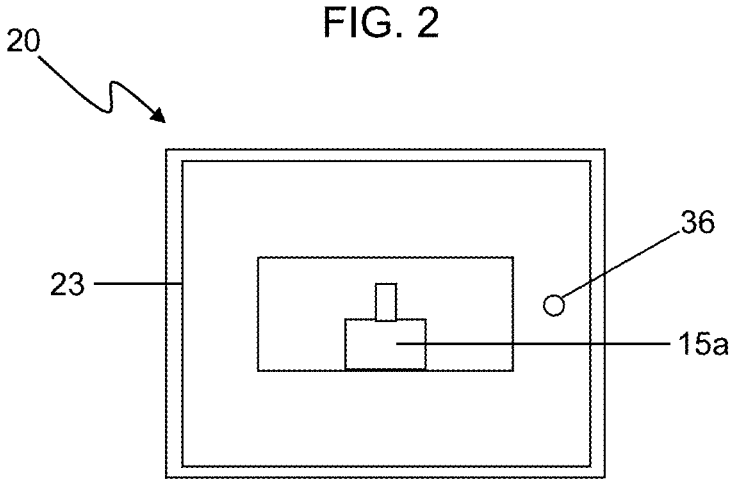
FIG. 3 shows an end on view of the waveguide shown in FIG. 1.

The microwave feed structure has a launcher 15a connected to a coaxial cable. The launcher has a dielectric sheath around a conducting pin. The launcher protrudes through the wall of the waveguide, and the pin projects from the end of the dielectric sheath. The microwave frequency electromagnetic energy is emitted from the pin into the waveguide. The pin is connected to the core of the coaxial cable and the dielectric sheath cooperates with a dielectric sheath in the coaxial cable to protect the pin and the coaxial core from an outer conductor of the coaxial cable. FIGS. 1 and 3 show the pin protruding from the dielectric sheath of the launcher.

Figure 2:
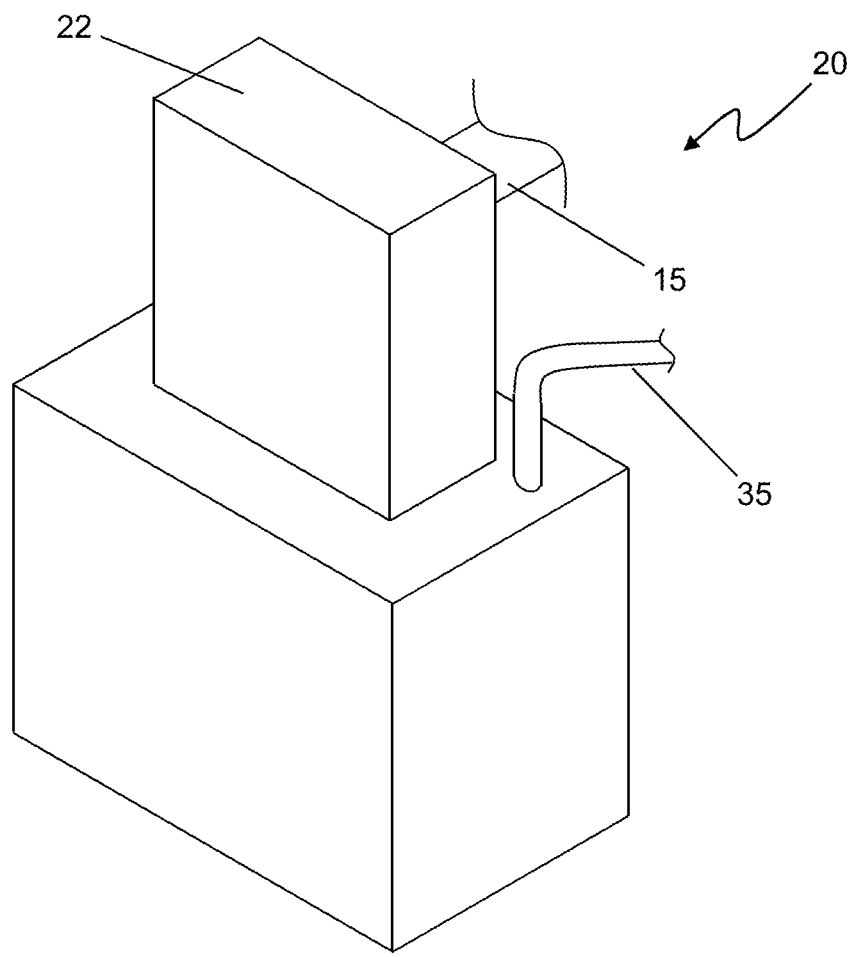
FIG. 2 shows a perspective view of the waveguide shown in FIG. 1.

A whole waveguide 20a is shown in FIG. 2. The end portion closest to the closed end 22 of the waveguide has the microwave feed structure 15 connected to it and has a rectangular cross-section of a smaller height and width than the end portion closest to the aperture 24 of the waveguide.

At the frequency of 14.5 GHz, the skin depth of the microwave frequency electromagnetic energy in suitable metals for the waveguide, for example aluminium, copper, silver or gold, is less than 1 μm. As such, the penetration of the microwave frequency electromagnetic energy is not the most limiting factor on the minimum thickness of the wall. A limiting factor may be the structural rigidity of the walls or the ability to support components such as the launcher. Due to the thickness required for a conductor, the conductor for the walls of the waveguide may be a coating on another material, e.g. plastic. The material onto which the conductor is coated would then dictate the shape and structure of the wave guide.

The skin depth effect limits the distance the microwave frequency electromagnetic energy emitted into the skin tissue travels before the energy is absorbed by the skin tissue thereby depositing the power in the skin tissue. The absorption of electromagnetic energy by biological tissue is measured using a specific absorption rate (SAR). The SAR is calculated using:

$$SAR = \int_{sample} \frac{\sigma(r)|E(r)|^2}{\rho(r)} dr,$$

where σ is tissue conductivity measured in S/m, E is the RMS electric field strength measured in V/m and ρ is the tissue density measured in kg/m$^3$. SAR is measured in Watts per kilogram (W/Kg). Tissue conductivity and density of skin tissue differ depending on whether the skin is dry or wet. Table 1 shows the properties of dry and wet skin when irradiated with microwave frequency electromagnetic energy at a frequency of 14.5 GHz. The value of the RMS electric field strength is dependent on the properties of the skin and the frequency of the electromagnetic energy.

TABLE 1

| Tissue properties for dry and wet skin at 14.5 GHz | | |
| --- | --- | --- |
| Property | Dry Skin | Wet Skin |
| Conductivity (S/m) | 13.27 | 14.082 |
| Relative permittivity | 26.88 | 28.621 |
| Loss factor (tan δ) | 0.61199 | 0.60995 |
| Wavelength (m) | 0.0038263 (3.8 mm) | 0.003709 (3.7 mm) |
| Depth of penetration (m) | 0.0021617 (2.2 mm) | 0.0021014 (2.1 mm) |

TABLE 1-continued

| Tissue properties for dry and wet skin at 14.5 GHz | | |
| --- | --- | --- |
| Property | Dry Skin | Wet Skin |
| Density (kg/m$^3$) | 1200 | 1200 |
| Specific heat capacity (J/kg · K) | 3600 | 3600 |

Figure 4:
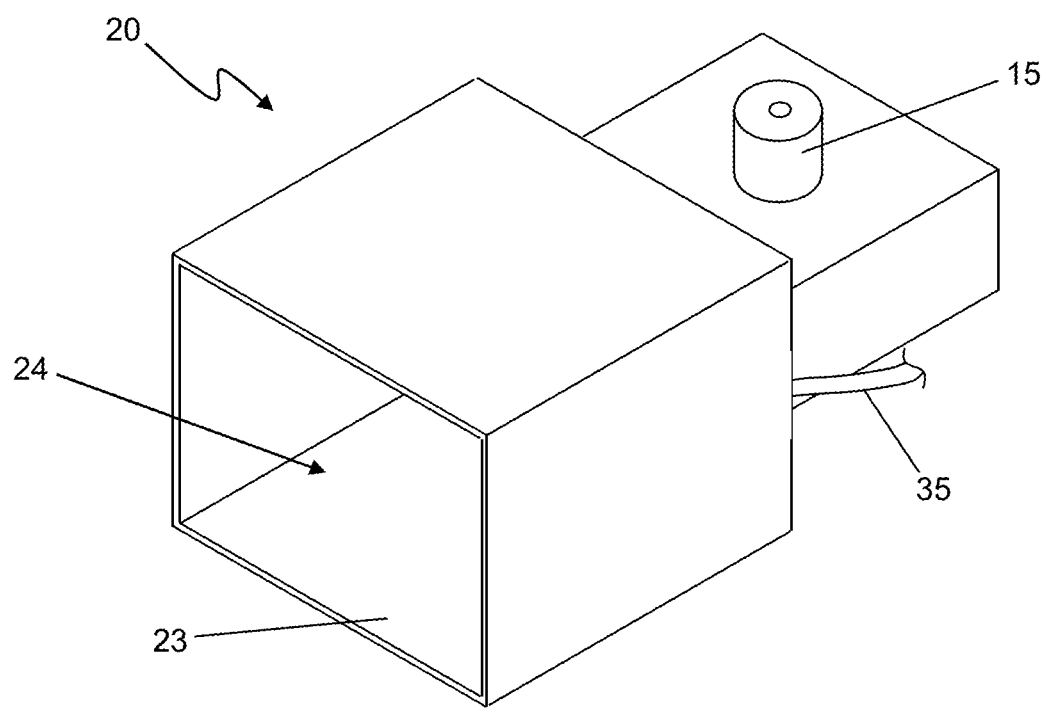
FIG. 4 shows a perspective view of the waveguide of FIG. 2 on its side.

The aperture 24 at one end of the waveguide 20a, as shown in FIG. 4, defines the exit from which the microwave frequency electromagnetic energy is emitted as an electromagnetic field from the waveguide. The dimensions of the aperture and the waveguide determine which modes will propagate in the waveguide by defining the cut-off frequency for transverse modes in the waveguide. The field pattern and distribution of the electromagnetic field is dictated by the modes propagating in the waveguide. If one mode is propagating in the waveguide the distribution of the electromagnetic field emitted from the aperture of the waveguide will be determined by the properties of that mode. If more than one mode is propagating in the waveguide the distribution of the electromagnetic field emitted from the aperture of the waveguide will be a hybrid of the properties and distribution of the modes propagating in the waveguide. With the correct dimensions the aperture and waveguide will be able to support modes higher than the fundamental mode, for example TE20 and or TE21 and/or support multiple modes simultaneously.

Figure 14:
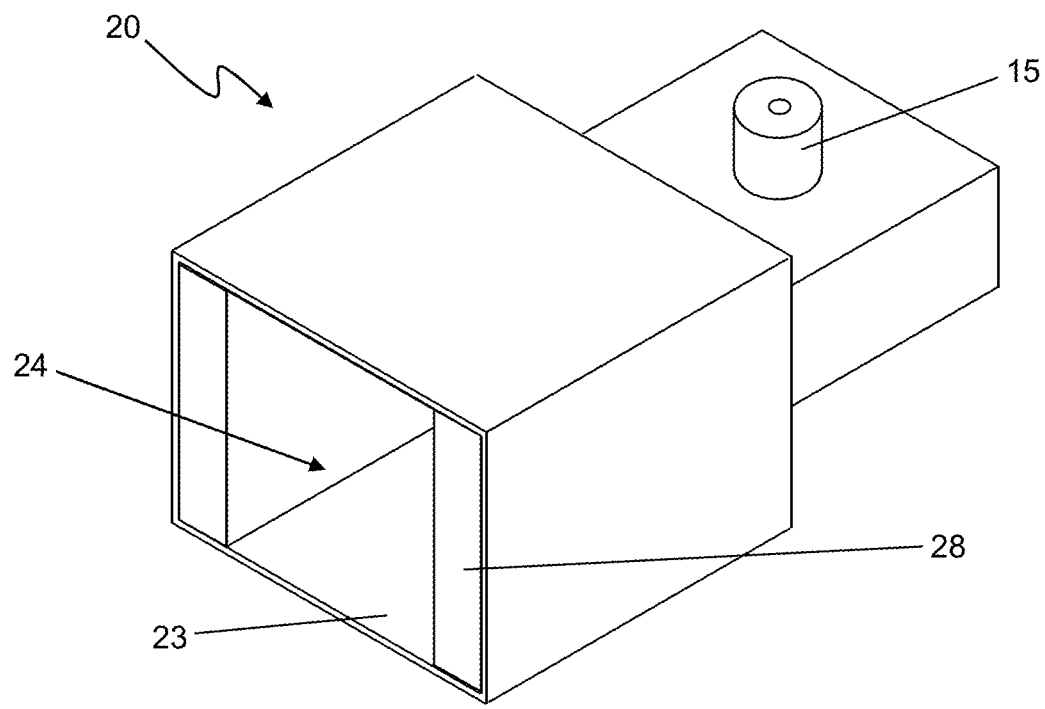
FIG. 14 shows a perspective view of another embodiment of the invention of the waveguide with dielectric or metamaterial inserts in the waveguide.

The shape of the aperture 24 can be altered, or a section of the interior wall 23 of the waveguide 20a be altered by use of a dielectric or metamaterial insert 28, as shown in FIG. 14 (not to scale), or coating to shield the section of the interior wall from the microwave frequency electromagnetic energy. If an insert or coating is applied, a pair of inserts or coated interior wall sections may be used. If a pair of inserts or coatings is used, they can be placed on opposing interior walls of the waveguide, such as those interior walls to which the electric field does not meet at a right angle, and extend from inside the waveguide to the open end of the waveguide at the aperture. If this is done, the inserts or coatings change the dimensions of the aperture and/or change the material on a pair of edges of the aperture and on sections of the interior wall of the waveguide. This alters the distribution of the microwave frequency electromagnetic energy within the waveguide and the distribution of the electromagnetic field emitted from the aperture.

In a preferred example, the inserts are dielectric blocks made from PTFE, PEEK or other suitable low loss material. The blocks may have a thickness of 5 mm, and may cover the entire interior wall section on which they are mounted. The side edge of each block that is exposed at the aperture may be covered by a reflector, e.g. a grounded conductive sheet, to prevent unwanted hot spots at the edges of the aperture. In combination with the dielectric blocks, the reflectors can ensure that the emitted field is substantially uniform.

Figure 5:
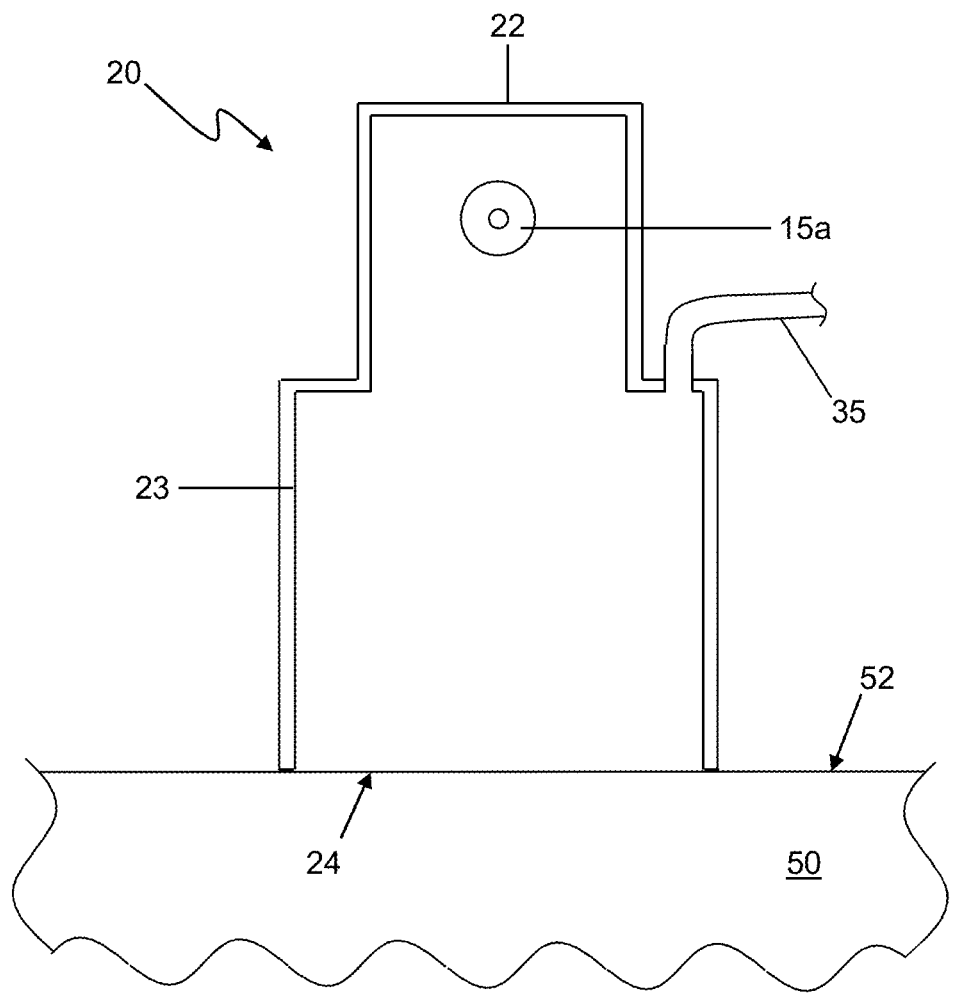
FIG. 5 shows a side view of a cross-section of the waveguide of FIG. 1 in use.

To irradiate skin tissue with microwave frequency electromagnetic energy the waveguide needs to be placed over a treatment region of skin tissue 50. The aperture can be placed against the surface 52 of the skin tissue, as shown in FIG. 5, or held above the surface with a separation between the aperture and the skin tissue.

Figure 6:
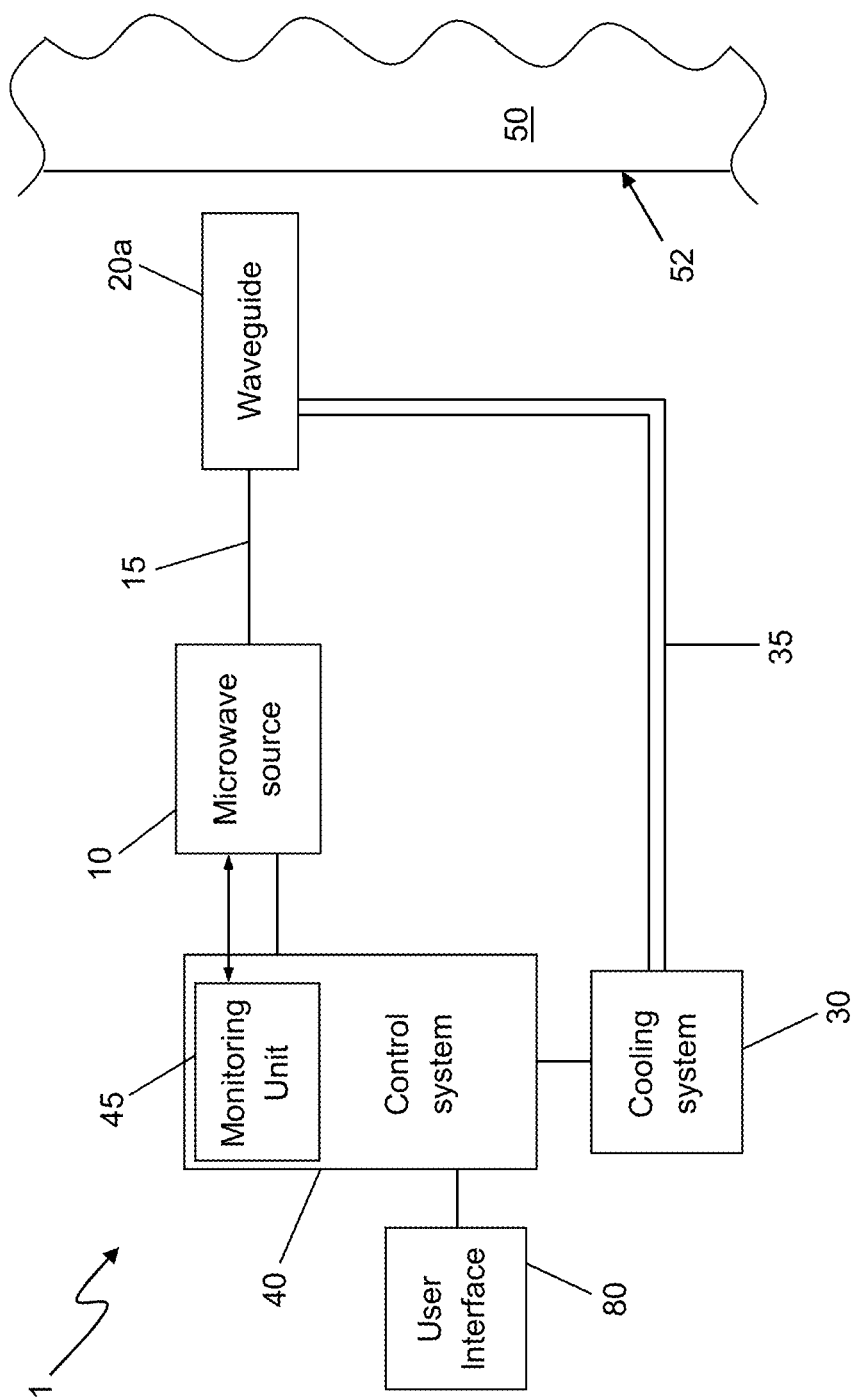
FIG. 6 shows a schematic representation of the skin treatment apparatus.

FIG. 6 shows an embodiment of the skin treatment apparatus 1. The waveguide is connected to the microwave source 10 and the cooling system 30. The waveguide is connected to the microwave source by the microwave feed structure 15 and to the cooling system by the cooling feed structure 35. The microwave source and the cooling system may also be connected to a control system 40. A monitoring unit 45 forms part of the control system and interacts with the microwave source as part of a monitoring system. The interaction between the monitoring unit and the microwave source is a two way process. The user interface 80 is connected to the control system 40 to allow system characteristics to be displayed to the user and/or to allow the user to control and adjust the system.

The microwave source 10 generates the microwave frequency electromagnetic energy which is then sent to the waveguide 20a though the microwave feed structure. The power generated by the microwave source may need to be adjusted if for example the power output from the microwave source drifts. To monitor the power generated, the microwave source is connected to a monitoring unit 45 which monitors the power received by the waveguide from the microwave source. The monitoring system can adjust the power generated if the power received by the waveguide deviates from predetermined parameters, for example the power output is drifting, the impedance mismatch between the generated microwave frequency electromagnetic energy is and the impedance of the waveguide or skin tissue 50 is causing inefficient signal generation, or may damage the apparatus 1. The monitoring system can assess the power sent to and received by the waveguide. Power received from the waveguide is monitored by detecting reflected power from the wave guide.

Figure 7:
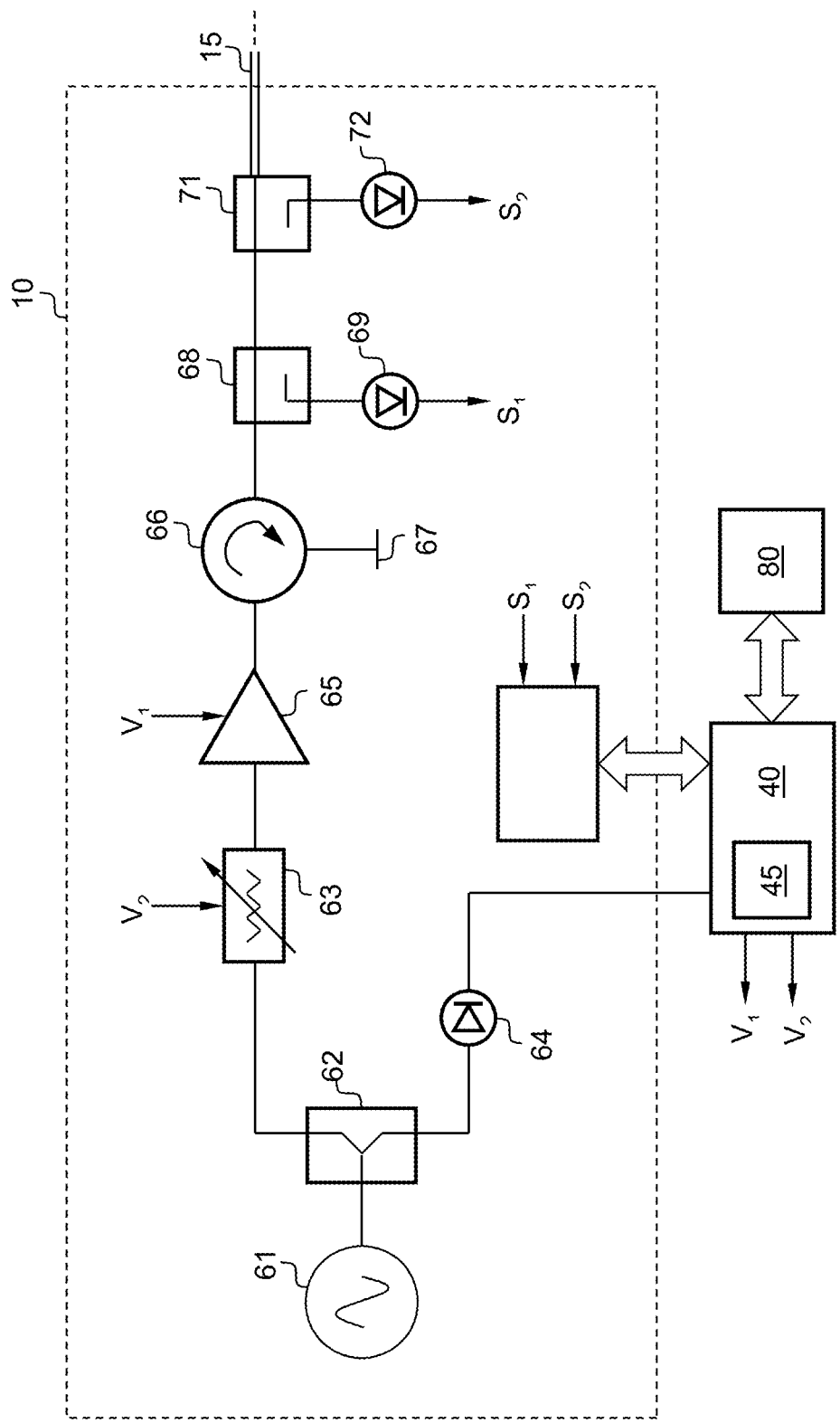
FIG. 7 shows a block diagram showing details of a microwave source for the skin treatment apparatus.

The microwave source is shown in FIG. 7. The microwave source comprises a source oscillator 61, such as a dielectric resonator oscillator, which produces low level energy at a frequency within the range deemed to be of interest for generating the microwave frequency electromagnetic energy, i.e. more than 10 GHz, preferably 14.5 GHz. The output from source oscillator is connected to a power splitter 62, which splits the source power into two parts, which may be balanced (or equal amplitude) or may be unbalanced, i.e. ⅓ and ⅔. A first part is fed into a detector 64, e.g. a diode detector, whose output is fed to a control system with a monitor unit 45 to monitor the status of the source oscillator to ensure that it is functioning correctly. The detector 64 may use a Schottky diode, i.e. a zero bias Schottky diode, or a tunnel diode. A second part is fed into a variable attenuator 63, which may be a PIN diode attenuator, whose attenuation is controlled by signal $V_2$ output from the control system.

The output from the variable attenuator is fed into the input port of a microwave power amplifier 65 which amplifies or boosts the signal produced by the source oscillator to a level that is useful for treating the biological (i.e. skin) tissue structures that are of interest. The microwave power amplifier 65 is controllable by signal $V_1$ output from the control system 40. A first port of a mm-wave circulator 66 is connected to the output stage of the power amplifier to protect the amplifier from high levels of reflected power which may result from an impedance mismatch between the biological tissue and the radiating section of the antenna. A second port of the circulator is connected to permit the forward (amplified) signal to travel to the antenna. Any reflected signals from the antenna therefore arrive at the second port, which is then diverted or directed to the third port. The third port of the circulator is connected to a power dump load 67. The impedance of the power dump load is selected such that all, or a high percentage, of the power reflected back into the second port of the circulator is diverted to the third port, where its energy is dumped into the load. In one embodiment the impedance of the dump load is 50Ω, but it is not limited to this value. Preferably the impedance is equal to the characteristic impedance of the microwave components used in the system.

The second port of the circulator is connected to a first directional coupler 68, which is configured as a forward power coupler and is used to sample a portion of the forward going power to enable the power level to be monitored. A coupling factor of between −10 dB and −30 dB may be used, which allows between 10% and 0.1% respectively of the main line power to be sampled. To preserve as much of the main line power as possible the coupling factor is preferably between −20 dB and −30 dB. The output from the coupled port of the first directional coupler is connected to a detector 69 (e.g. diode detector) which converts that output to a DC or lower frequency AC signal $S_1$ and feeds it to the control system. The detected forward power level may be processed by the monitoring system and displayed on the user interface. The location of first directional coupler is not limited to the second port of circulator, i.e. it may be connected to the first port of circulator.

The main line output from the first directional coupler is fed into the input port of a second directional coupler 71, which is configured as a reflected (or reverse) power coupler and is used to sample a portion of the reflected power to enable the level of returned or reflected power to be monitored and provide an indication of the impedance match (or mismatch) between the biological tissue and the radiating portion (distal tip or aerial) of the needle antenna. The output from the coupled port of the second directional coupler 71 is connected to a detector 72 (e.g. diode detector, homodyne detector or heterodyne detector) which converts that output to a DC or lower frequency AC signal $S_2$, which may contain magnitude or magnitude and phase information, and feeds it to the monitoring unit 45. The detected reflected power level may be processed by the monitoring unit and displayed on the user interface 80. The first and second directional couplers may, for example be microstrip directional couplers.

The monitoring unit may be arranged to calculate and display, on the user interface via the control system 40, the net power being delivered into the tissue, e.g. by subtracting the reflected power level from the forward power level, taking into account the loss (insertion loss) of a delivery cable or PCB track (e.g. a flexible coaxial cable, a flexible/twistable waveguide, a microstrip line, a coplanar line, or a low-loss coaxial cable) connected between the output port of the second directional coupler and the input to the waveguide 20a, and the insertion loss of the waveguide itself, i.e.

$$P_{net} = P_{forward} - P_{ch_{loss}} - P_{ant\_loss} - P_{reflected},$$

where $P_{net}$ is net power, $P_{forward}$ is forward power, $P_{ch\_loss}$ is delivery channel loss, $P_{ant\_loss}$ is antenna structure loss, and $P_{reflected}$ is loss due to reflected power caused by an impedance mismatch between the radiating section of the antenna and the biological tissue load.

The monitoring unit, which may be a microprocessor, microcontroller, combined microprocessor and digital signal processor (DSP) unit, a single board computer or a single board computer and a DSP unit, may be used to control the functionality and operation of the apparatus. The monitoring unit may be responsible for controlling the variable attenuator 63, checking the status of the source oscillator 61, measuring the forward and reflected power levels, calculating the net power, generating user information and flagging up error conditions. The user interface 80 may include an input/output device arranged to enable the user to enter information into the system and for displaying parameters that may be of interest to the user. The input/output device may be a touch screen display unit, a keyboard/keypad and a LED/LCD display, LED segments and switches, or any other suitable arrangement for an input/output device.

The apparatus 1 may include a DC isolation barrier (not shown here) connected between the generator and the patient to prevent a DC voltage path between the generator and the patient. Such a barrier may take the form of a microstrip capacitor or two sections of waveguide sandwiched between a sheet of low loss dielectric material, for example, a thin layer of microwave ceramic, Kapton® sheet or PTFE.

Returning to FIG. 6, the cooling system 30 sends pulses of cooling medium, e.g. liquid or gas coolant, to the waveguide 20*a*. The cooling system sends pulses of cooling medium as according to a cooling regime. The cooling regime may comprise parameters that affect cooling, such as type of coolant, flow rate, number of pulses of cooling medium dispatched in a predetermined period of time, etc. The cooling regime is set to dictate the cooling profile which is to be established in the treatment region of the skin tissue 50. A change in the cooling regime will change the properties of the cooling profile, for example the gradient, depth penetration and/or temperature range can be changed by altering the cooling regime. The time gap between the pulses and the duration of the pulses are primary factors which alter the cooling regime and therefore the cooling profile.

The microwave source 10 and/or the cooling system are controlled by the control system 40 which can control the properties of the microwave frequency electromagnetic energy generated by the microwave source, for example the power, frequency and/or amplitude of the microwave frequency electromagnetic energy. The control system can also control the cooling regime or the length of the pulses of cooling medium and/or the time gap between the pulses of cooling medium.

The control system 40 is connected to a user interface 80 which has a display which displays properties associated with the microwave frequency electromagnetic energy and/or the cooling regime. The user interface can also be used to adjust predetermined properties of the microwave frequency electromagnetic energy and/or the properties of the cooling regime or cooling profile.

Figure 8:
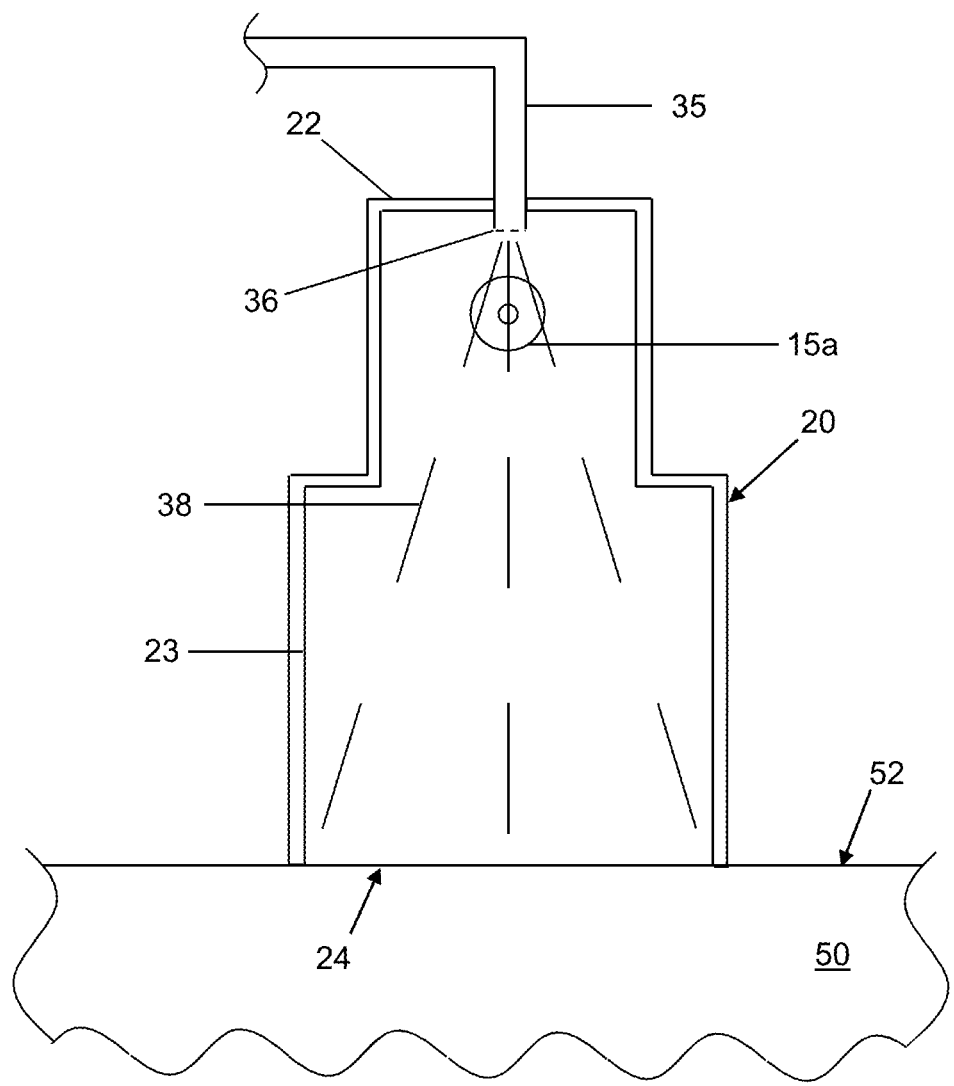
FIG. 8 shows side view of a waveguide in use of an alternative embodiment of the invention.
Figure 12:
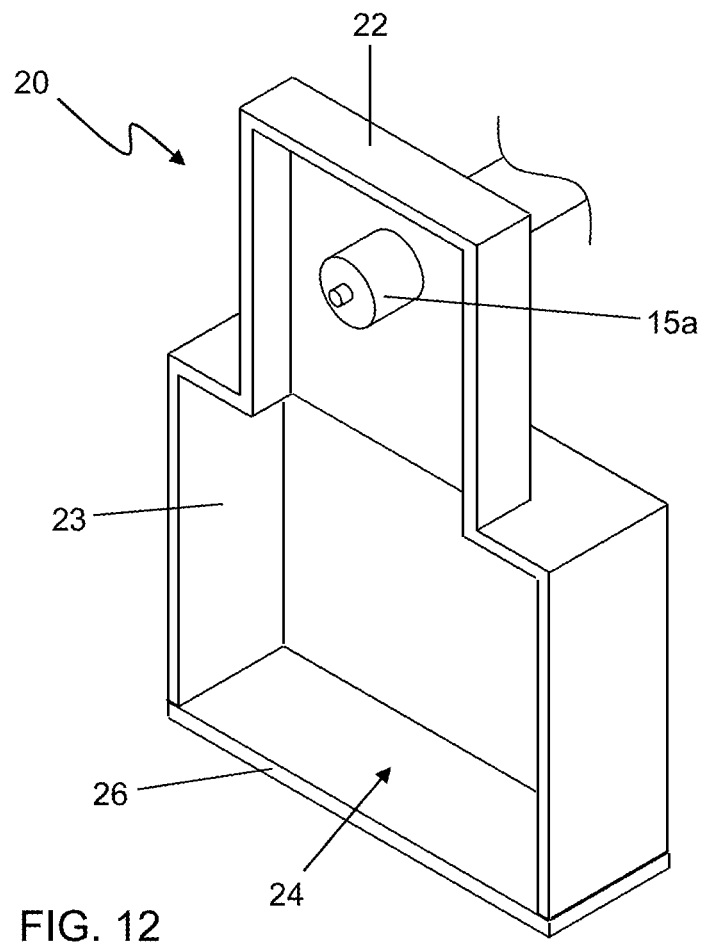
FIG. 12 shows a perspective view of another embodiment of the invention of a cross-section of a waveguide with a cover over the aperture.

An alternative embodiment of the cooling feed structure 35 feeding into the waveguide 20*a* is shown in FIG. 8. In this embodiment there is a pipe connected to a nozzle 36 which launches the pulses of cooling medium 38 into the waveguide to the aperture 24 and onto the surface 52 of the treatment region of skin tissue 50. In the embodiment of the applicator 20 shown in FIG. 12, shows an embodiment in which the aperture has a cover 26. If the aperture has a cover and the cooling medium is to be applied to the skin tissue through the waveguide, the cover needs perforations to allow the cooling medium to pass through the cover to the surface of the skin tissue.

Figure 9:
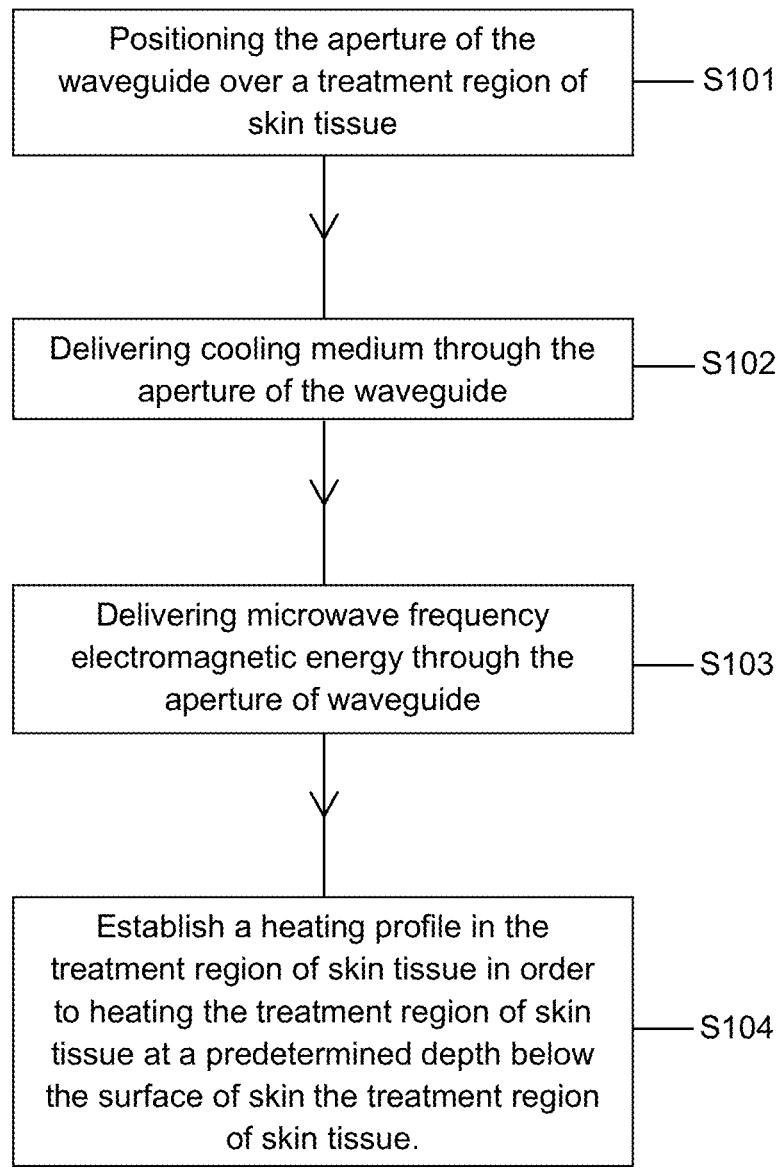
FIG. 9 shows a flow diagram of a method of enacting the invention.

As shown in FIG. 9, when an ablation or heating zone is to be formed at a predetermined depth below the surface of a treatment region of skin tissue the aperture of the waveguide is placed over the treatment region of skin tissue, S101. The cooling system 30 delivers the cooling medium, via the cooling feed structure, to the waveguide and through the aperture to establish a cooling profile in the skin tissue, S102. The skin tissue is then irradiated with an electromagnetic field produced by microwave frequency electromagnetic energy being supplied into the waveguide through the microwave feed structure 15 from the microwave source 10 to establish a heating profile in the treatment region, S103. The cooling regime is continued whilst the microwave frequency electromagnetic energy is being supplied to the waveguide. The cooling profile and heating profile cooperate to cause the skin tissue from the surface of the skin tissue to a predetermined depth within the skin tissue to be unaffected by the irradiation with electromagnetic energy. Below this depth a region is established in which the heating is sufficiently greater than the cooling that an ablation or heating zone is formed which is capable of stopping the tissue from functioning and/or denaturing proteins, S104. At a depth below the ablation or heating zone, the heating is insufficient to cause a reduction in functionality of the skin tissue 50. This can be because of the dispersal of the electromagnetic energy due to the skin depth effect and/or because the cooling is sufficient to cancel out the heating to produce heating less than a temperature which might or is likely to cause a harmful effect on the skin tissue.

Figure 10A:
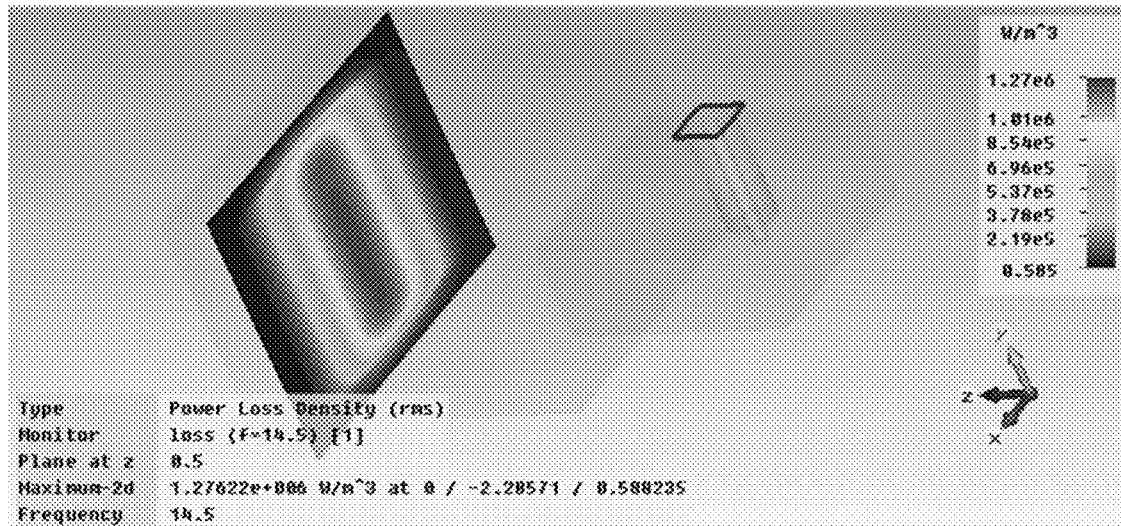
FIGS. 10A and 10B show a horizontal and vertical field distribution of microwave frequency electromagnetic field emitted from the aperture of the waveguide.
Figure 10B:
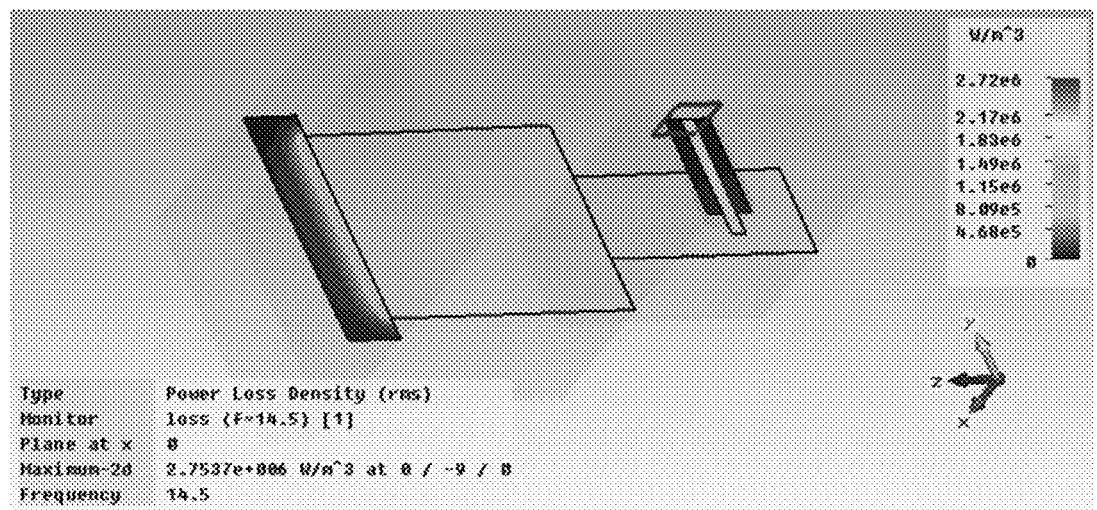

FIG. 10A and FIG. 10B show the electromagnetic field distribution in the treatment region of skin tissue of the electromagnetic field emitted from the aperture 24 of the embodiment shown in FIG. 1 of a rectangular waveguide 20*a*. The aperture is rectangular and has a long and a short axis. FIG. 10A shows the horizontal field distribution of the field across the plane of the aperture. The field distribution shown in FIG. 10A has a cosine distribution along the long axis of the aperture with a minimum at either end of the long axis and a maximum at the centre of the axis. The distribution of the field along the short axis is steep at the ends of the short axis and has a shallow domed central distribution extending to a boundary region at each end of the short axis. This shape is followed along the distribution on along the long axis with the steep sections reducing in size and the dome becoming shallower towards the ends of the long axis. The distribution causes the field to have most energy at the centre and decrease from towards the edges of the aperture. An ideal distribution of the electromagnetic field would be a step distribution in the long and short axes having minima at the ends of the axes and maxima at all other points.

The power distribution of the electromagnetic field mirrors the distribution of the field. However, as the power of the field is proportional to the square of the field strength the power distribution of the field has a cosine squared distribution along the long axis of the aperture being at a minimum at the ends of the long axis. The power distribution of the electromagnetic field along the short axis is the same as the field distribution.

Due to the orientation of the field shown in FIG. 10A, the field has a peak running along the short axis of the aperture at the centre of the long axis. This is caused by the orientation of and shape of the microwave frequency electromagnetic energy launcher 15*a*. If the launcher 15*a* position is changed or the launcher shape is modified the distribution will take a different form. The width of the waveguide 20*a* at the launcher also affects the shape of the electromagnetic field distribution. The width could, at least in one example, be described or defined as the direction that is perpendicular with respect to the electric field.

FIG. 10B shows the vertical electromagnetic field distribution from the aperture 24 into the treatment region of the skin tissue 50 at the centre of the long axis of the rectangular aperture in a plane perpendicular to the plane of the aperture parallel to the short axis of the aperture. In concordance with the field distribution in the plane of the aperture shown in FIG. 10A, the field distribution across the aperture matches the field distribution of the short axis of the aperture. The field distribution has a peak at the aperture and decreases as the distance from the aperture and the waveguide increase. The field strength decreases in an exponential manner.

The distribution and shape of the electromagnetic field emitted from the aperture of the waveguide as shown in FIG. 10A and FIG. 10B are changed if the dimensions of the waveguide change. The dimensions of the waveguide are changed if an insert 28 or coating on an interior wall 23 of the waveguide is used, the waveguide is a different shape or material, for example due to skin tissue entering the waveguide. Skin tissue may be present in the waveguide if it bulges through the aperture if the waveguide is pushed onto the treatment region of skin tissue when the aperture has no cover. For this reason, the cover 26 is used to maintain the dimensions of the waveguide when in use and to stop material entering the waveguide.

Figure 11:
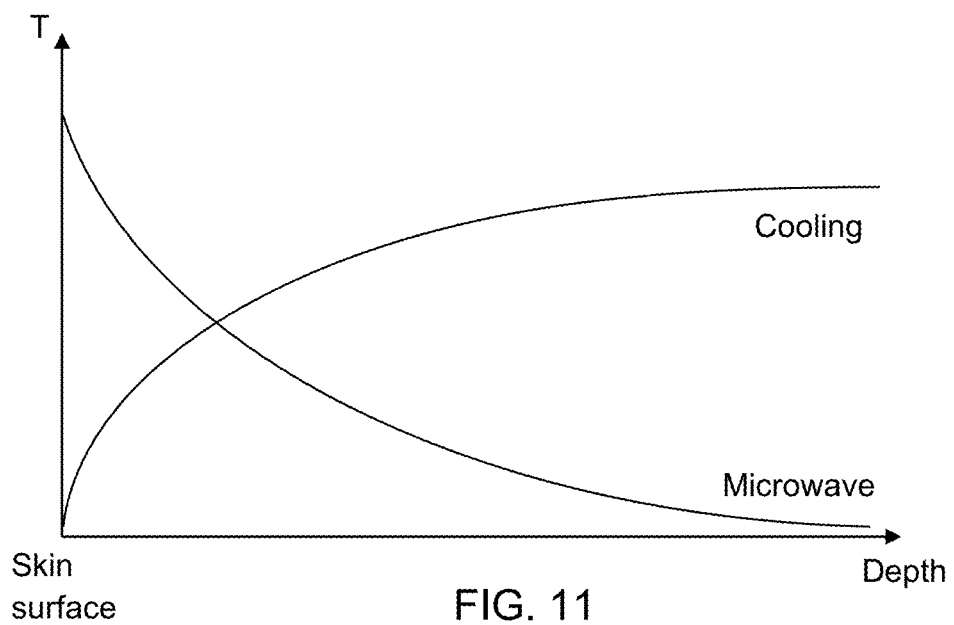
FIG. 11 shows a representation (not to scale) of the first temperature profile due to cooling and the second temperature profile.

FIG. 11 shows overlaid examples of the temperature variation with depth associated with the cooling profile and the heating profile. The heating profile shows an exponential decrease in temperature as the depth of penetration into skin tissue increase. The temperature decreases from a finite maximum heating value to ambient temperature for the skin tissue 50. For a given frequency the depth penetration of heating cannot be altered due to the skin depth effect, but the temperature range can be changed by changing the power of the microwave frequency electromagnetic energy. The power is increased by increasing the amplitude of the microwave frequency electromagnetic energy and decreased by decreasing the amplitude. The cooling profile has a minimum temperature and increases towards ambient skin tissue temperature in a curve, which at least approximates to an exponential-like curve. The depth and the temperature range of the cooling profile can be adjusted by adjusting the amount of cooling medium applied to the surface 52 of the skin tissue and/or by adjusting the time between cooling medium pulses. By adjusting the temperature profiles an ablation or heating zone can be formed at a desired depth between the surface of the treatment region of skin tissue and the maximum penetration depth of the microwave frequency electromagnetic energy.

FIG. 13 shows a circular waveguide 20a with a stepped change in diameter along the length of the waveguide. A circular waveguide would behave in a similar way to a rectangular waveguide, although the fundamental mode and therefore the lowest cut-off frequency would be different. All the features which can be used with the rectangular waveguide described above can be applied to a circular waveguide with and necessary adjustments made to the features for them to work in the intended way but in the circular waveguide. If inserts 28 or coatings are used on sections of the interior wall 23 of the circular waveguide a number of pairs of inserts or coatings can be placed around the circumference of the waveguide at opposite positions around the circumference.

Figure 15A:
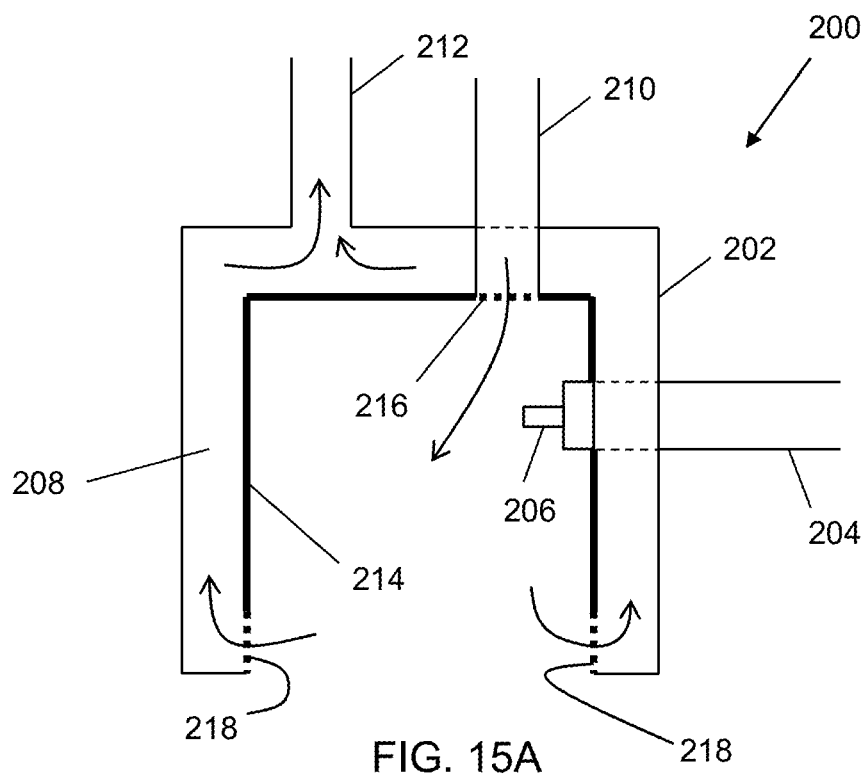
FIGS. 15A and 15B show a cross-sectional view and a top view respectively of a waveguide applicator that is another embodiment of the invention.
Figure 15B:
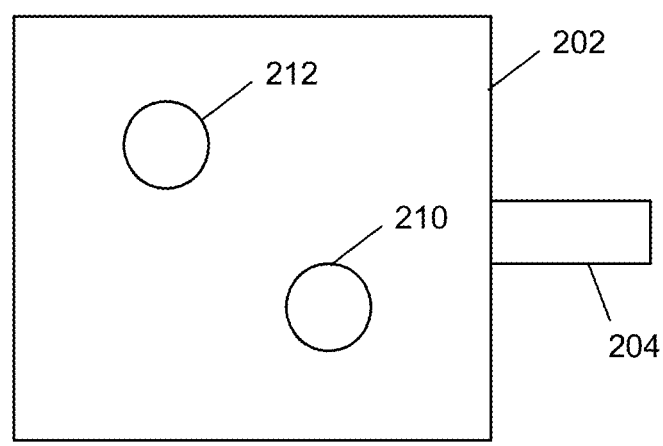

FIG. 15A is a cross sectional view through a waveguide applicator 200 that is another embodiment of the invention. FIG. 15B shows a plan view of the same device. In this embodiment, the waveguide is a rectangular waveguide having a conductive inner surface for guiding the microwave energy in the same manner as discussed above. The waveguide applicator 200 therefore comprises a rectangular waveguide body 202 which in this embodiment has a coaxial feed 204 mounted on a side surface thereof. As discussed above, the coaxial feed 204 includes an inner conductor 206 that protrudes from a distal end of the coaxial structure to form an antenna for launching microwave energy into the waveguide cavity.

In this embodiment, the waveguide body 202 has a hollow passage 208 in its side and end walls, which forms a passageway for recirculation of coolant material, e.g. gas or liquid. The coolant is introduced through an input pipe 210 and removed from the passage 208 via an outlet pipe 212. The inlet and outlet pipes 210, 212 may be connected to a circulation system (not shown), e.g. comprising a pump, heat exchanger, or the like, for refreshing or regulating the temperature of the coolant.

The inner walls of the waveguide cavity have a conductive surface 214. The conductive surface 214 is porous, e.g. formed from a mesh, over an aperture 216 where the inlet pipe 210 joins the waveguide cavity. One or more outlets 218 are formed at the bottom of the microwave cavity (where it abuts a skin surface in use) which provide a fluid communication path from the interior of the waveguide cavity into the passage 208. These apertures may also be covered by a porous layer made of electrically conductive material, e.g. a mesh or the like. Holes in the mesh for the apertures 216, 218 may be dimensioned to prevent leakage of the microwave energy, e.g. by being much smaller than the wavelength of the microwave energy in the cavity, e.g. equal to or less than one tenth of the wavelength.

FIG. 16 shows a cross-sectional view of a waveguide applicator 220 that is another embodiment of the invention. In this example, the waveguide body has a structure similar to that disclosed with respect to FIGS. 1 to 5. However, the waveguide body in this example also includes a deformable contact rim 222 mounted around the entrance to the waveguide, which is the region that contacts a skin surface in use. Using a deformable element in this location ensures that a good consistent contact is made with the skin surface, and may also improve patient comfort.

The deformable contact rim 222 may be a disposable element, i.e. may be detachable for disposal or sterilisation, as required. The deformable contact rim 222 may be formed from any suitable biocompatible material, e.g. silicone rubber, foam, dielectric clay, or the like. In order to assure proper propagation of the microwave energy through and out of the waveguide, the inner surfaces of the deformable contact rim 222 may have a layer of metallisation 224 formed thereon, which is in electrical communication with an electrically conductive inner layer 226 of the waveguide itself.

The deformable contact rim may have the same cross sectional shape as the mouth of the waveguide applicator. However, in other examples, the shape of the deformable contact rim may be different, e.g. to make it suitable for mounting over a specific region of skin, e.g. above or below a patient's eye or mouth.

FIG. 17A is a cross sectional view through a waveguide applicator 228 that is another embodiment of the invention. In this example, a waveguide loading unit 230 is mounted in the mouth of the waveguide, e.g. in the region that contacts a skin surface in use. The loading unit 230 may be formed of a dielectric material having properties selected to shape the field emitted by the waveguide. The properties may include the material of the loading unit, i.e. its dielectric constant, as well as physical properties, e.g. its shape or configuration. The loading unit may be arranged to focus or otherwise shape the emitted microwave field to match a desired region of treatment on the skin surface.

In the example shown in FIG. 17A, the waveguide has a circular cross section, and the loading unit 230 is a dielectric disc that is mountable, e.g. by interference fit or the like, in the mouth of the waveguide. The dielectric disc has a plurality of holes 232 formed therein. The diameter of the holes may vary across the surface of the disc depending on the desired energy profile to be transmitted. In this example, the holes may be dimensioned so that the applied energy is in the form of a pattern of dots, e.g. similar to the fractionated delivery of energy used in conventional techniques (lasers, radiofrequency, micro needles). Embodiments of the present invention may thus be adapted to selectively perform either uniform treatment, where microwave energy is delivered as a blanket over a given area, or in a fractionated manner, where energy is delivered to an array of discrete locations.

The loading unit may be a detachable or disposable element, e.g. to enable different types of treatment to be available from the same waveguide applicator.

Figure 22A:
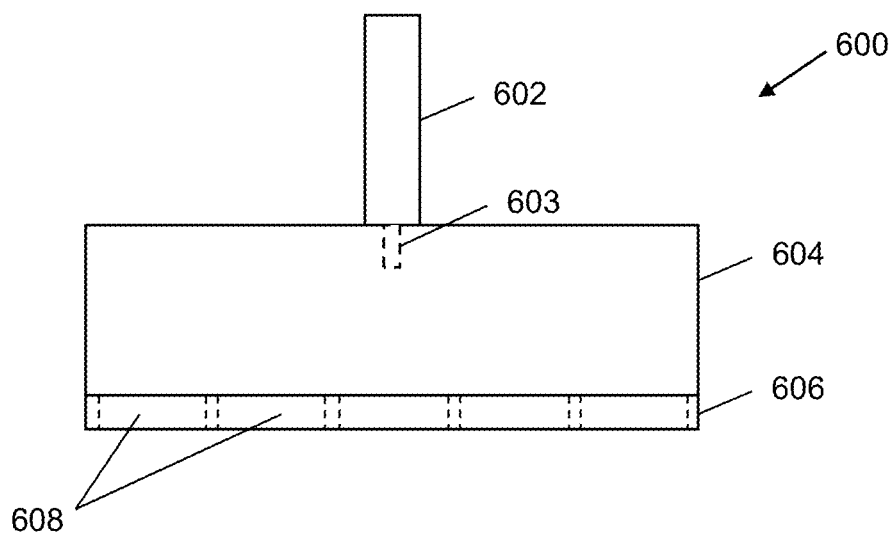
FIG. 22A shows a schematic side view of an applicator for fractionated microwave energy delivery for use in another embodiment of the invention.
Figure 22B:
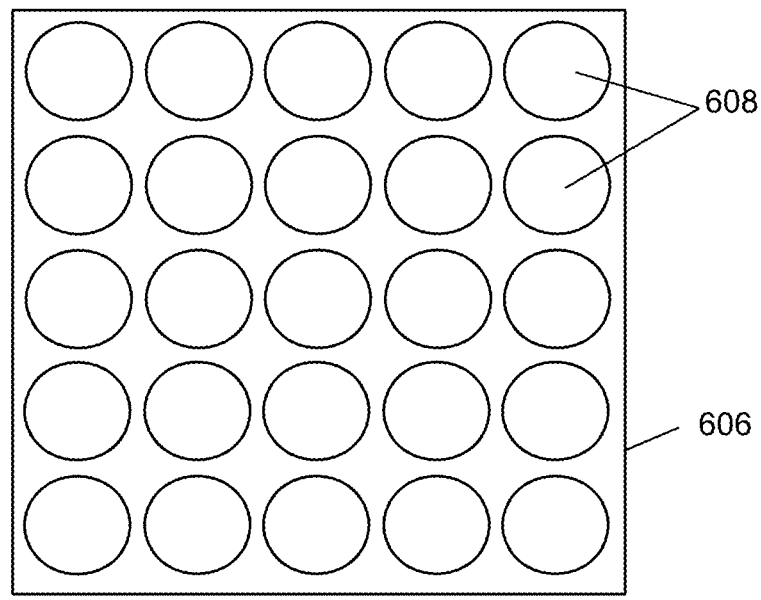
FIG. 22B is a bottom plan view of the applicator shown in FIG. 22A.

FIGS. 22A and 22B show another example of a loaded waveguide type applicator 600, which is adapted to deliver fractionated microwave energy, i.e. an array of discrete energy spots or dots. In this example, the applicator 600 comprises a waveguide 604 that defines a cavity through which microwave energy can propagate. A coaxial feed cable 602 is connected to a rear surface of the waveguide 604. An inner conductor 603 of the feed cable 602 protrudes into the cavity to form an antenna for launching microwave energy into the waveguide 604. In one example, the feed cable 602 is attached to the waveguide 604 via an SMA connector. The feed cable 602 may interface with the waveguide at the geometric centre of the top surface. The other end of the cable 602 is connected to a suitable source (not shown) that generates the microwave energy.

The front surface of the cavity defines an aperture that is covered by a loading unit 606. In this example, the loading unity comprises a sheet of dielectric having an array of holes 608 formed therein. The holes represent discrete radiating points so that the applicator delivers the microwave energy in a fractionated manner. The geometric arrangement and dimensions of the holes 608 may be selected to provide a desired treatment pattern.

FIG. 18 shows a cross sectional view of a waveguide applicator 240 that is another embodiment of the invention. In this example, the waveguide applicator 240 has a waveguide body 242 having a similar structure to the example discussed above with respect to FIGS. 1 to 5. Microwave energy is launched into the waveguide body 242 by a coaxial feed 244. In this example, an imaging device 246 is mounted on the back surface of the waveguide body 242, and arranged so that its field of view 248 captures the window of the waveguide body that is positioned at a skin surface when in use.

The imaging device 242 may be a camera mounted to give visual feedback of the skin surface during treatment. The camera may be arranged to capture visible light, whereby it can be used to ensure that the device is correctly located. A light source (not shown) may also be mounted on the inside of the cavity to provide illumination.

Alternatively or additionally, the camera may be arranged to capture infrared radiation. This can be used to monitor the thermal effect of treatment, e.g. in terms of the shape of the treated area and its temperature. In turn, this can be used as part of a feedback control system to control the level of power delivered into the waveguide applicator. An example of how this can be achieved is shown in FIGS. 21A and 21B.

Figure 21A:
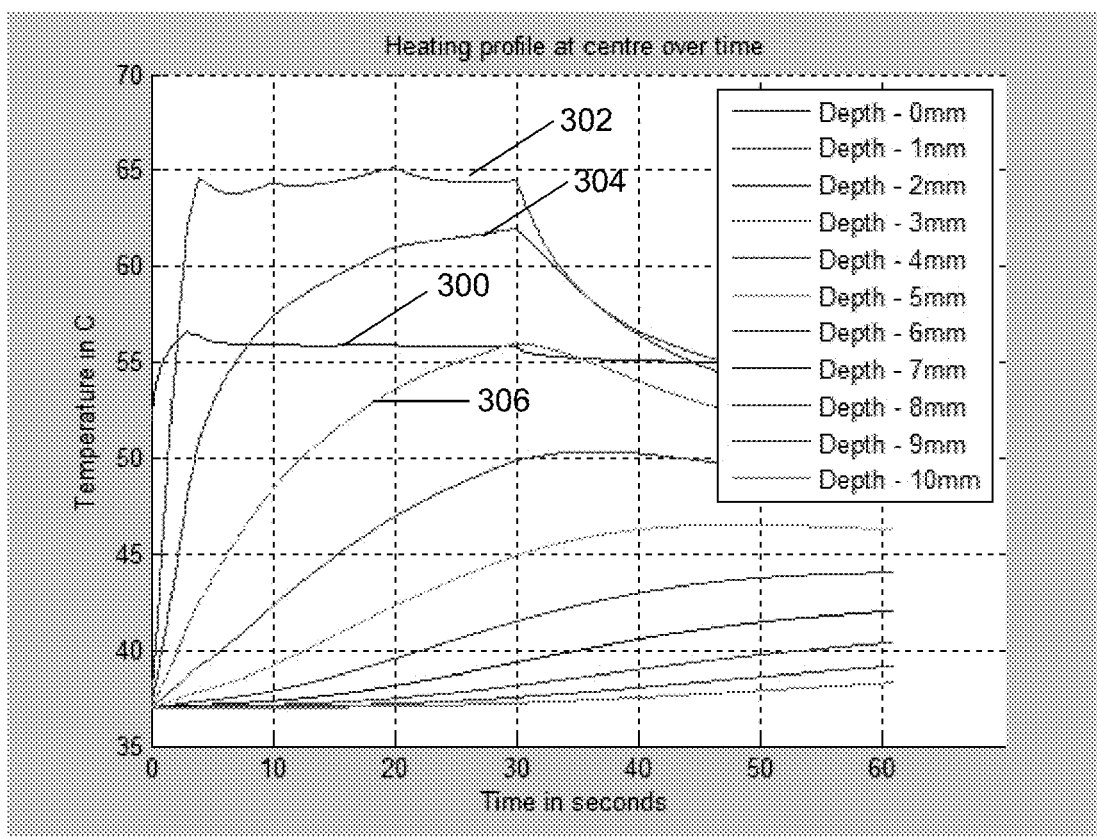
FIG. 21A shows a graph of heating profile over time.
Figure 21B:
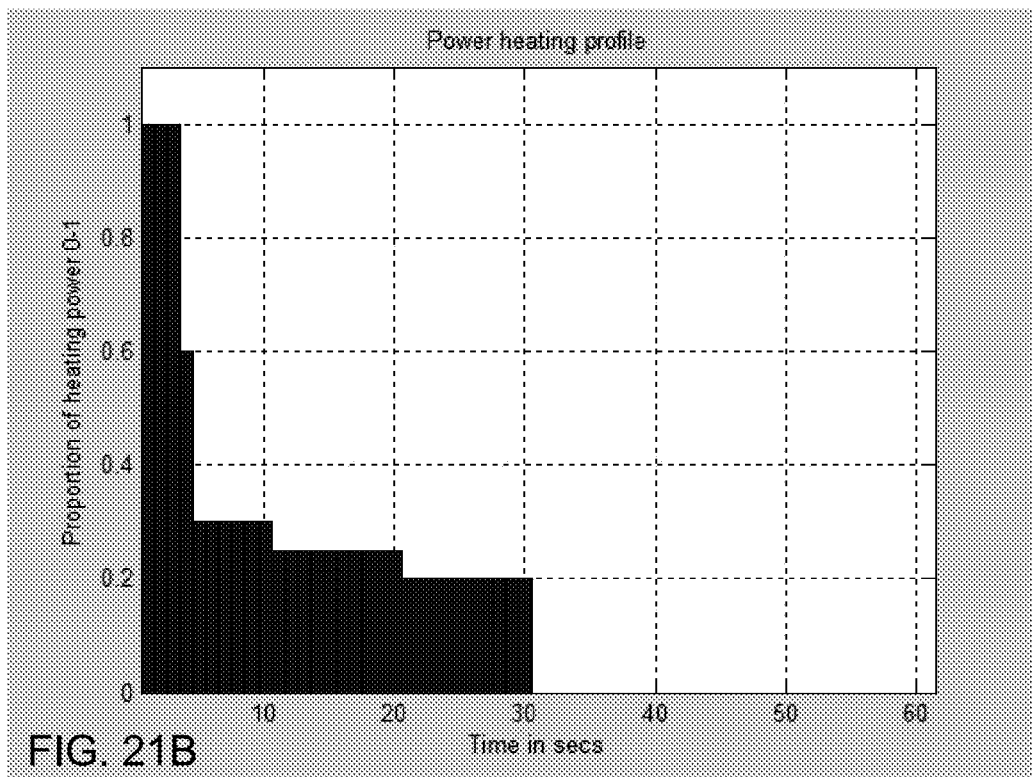
FIG. 21B shows a power delivery profile corresponding to the graph shown in FIG. 21A.

FIG. 21A shows a graph of heating profile in the skin at the centre of the region covered by the waveguide applicator in a simulation using the device discussed with respect to FIG. 18. The camera is suitably calibrated (as known in the art) to enable it to effectively measure temperature at the skin surface, which corresponds to line 300 on the graph in FIG. 21A. The power delivery system was arranged in a feedback loop to maintain the temperature of the skin surface (line 300) at around 55° C. for 30 seconds, before power was switched off. The power delivery profile is shown in FIG. 21B, where it can be seen on the basis of the detected temperature the proportion of delivered power was stepped back several times through the 30 second treatment period. FIG. 21A shows that the temperature of the skin and a depth of 1 mm (line 302) rose rapidly and was maintained at around 65° C. The temperature at a depth of 2 mm (line 304) gradually rose to an exceeded 60° C. during the treatment period. The temperature and a depth of 3 mm (line 306) rose gradually to around 55° C. towards the end of the treatment period. This example shows that temperature monitoring using an infrared camera can ensure that the skin surface is maintained at a temperature below which thermal damage occurs, whilst ensuring that the temperature below the surface of the skin can reach a desired treatment temperature.

FIGS. 19A and 19B show two schematic examples of waveguide applicators 250, 252 which are shaped to conform with a region of skin. In the examples shown in FIGS. 19A and 19B, the waveguide applicators 250, 252 are shaped to fit in regions above and below a patient's eye 254. In other examples, the applicators may have a shape that fits above or below a patient's mouth. By shaping the waveguide applicator so that it is purpose fitted to an anatomical region of a patient's body, treatment can be focused in regions where it is required. In both of the examples shown in FIGS. 19A and 19B, the waveguide applicator 250, 252 comprises a conformal applicator body 256 that is connected to receive power via a cable 258. As discussed above, these applicators can be used with a cooling medium, which may be a cream or spray applied in advance to the surface of skin, or maybe a layer of cooling material formed in the conformal body 256.

Figure 20A:
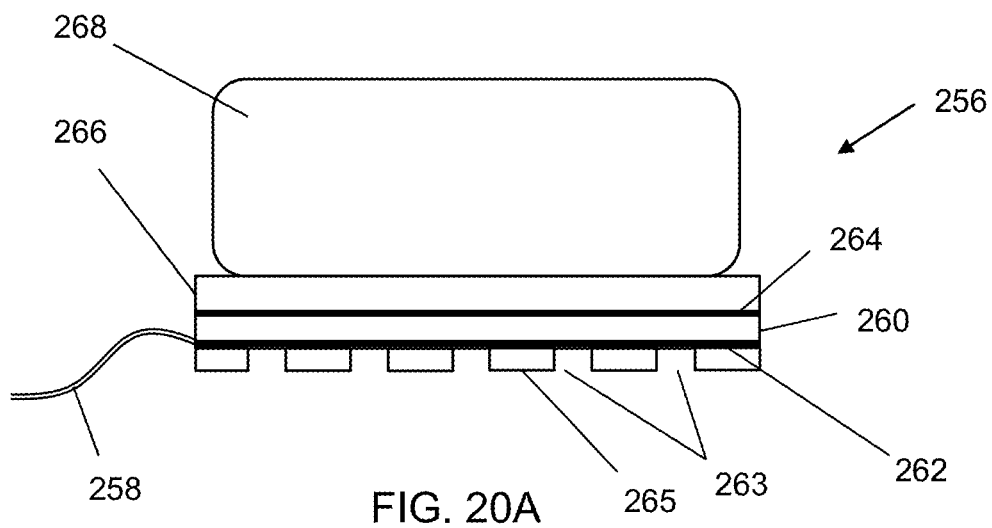
FIG. 20A shows a cross-sectional view of a shaped flexible waveguide applicator that is an embodiment of the invention.
Figure 20B:
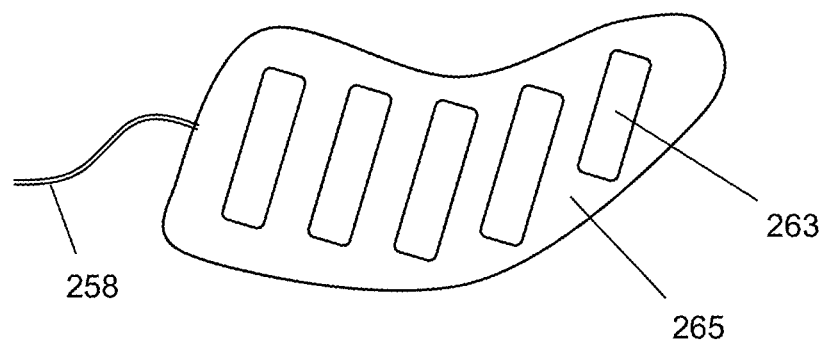
FIG. 20B shows a bottom view of the shaped flexible waveguide applicator shown in FIG. 20A.

FIG. 20A shows a cross sectional view through one example of a conformal applicator. The waveguide structure in this example is formed as a slotted microstrip antenna. The micro strip antenna comprises a layer of flexible dielectric material 260 that has a first conductive layer 262 formed on a first surface thereof and a second conductive layer 264 formed on a second surface thereof. The first conductive layer 262 is connected to an inner conductor of a coaxial feed line 258. The second conductive layer is grounded by electrically connecting it to an outer conductor of the coaxial feed line 258. A front layer of dielectric material 265 is mounted on top of the first conductive layer 262, and has a plurality of slots 263 formed therein which permit energy conveyed by the microstrip antenna to be delivered into tissue. As shown in FIG. 20B, the flexible dielectric layer and the configuration of the slots 263 can be arranged in a manner to conform with a region of skin to be treated.

The front layer of dielectric material 265 may have a tacky or adhesive property or coating to assist in retaining the applicator in position.

A backing layer 266 is attached behind the second conductive layer. This may be a heat sink or cooling layer that has the effect of counteracting the energy delivered at the surface of the skin. A handle 268 is mounted on the backing layer 266 to allow the device to be easily applied.

The invention might be used in ways that are in addition to, or alternative to, those described above. For example, the invention might find use in the treatment of one or more of, or a combination of: skin tissue just beneath a surface of the skin or on or within a skin surface; cancer or skin cancer; malignant or benign cancer or skin cancer; tumours or skin tumours; malignant or benign tumours or skin tumours; lesions; keratosis; dermatitis; hair removal; collagen shrinkage; wrinkle reduction; and/or tattoo removal.

Although a few preferred embodiments have been shown and described, it will be appreciated by those skilled in the art that various changes and modifications might be made without departing from the scope of the invention, as defined in the appended claims.

All of the features disclosed in this specification (including any accompanying claims, abstract and drawings), and/or all of the steps of any method or process so disclosed, may be combined in any combination, except combinations where at least some of such features and/or steps are mutually exclusive.

Each feature disclosed in this specification (including any accompanying claims, abstract and drawings) may be replaced by alternative features serving the same, equivalent or similar purpose, unless expressly stated otherwise. Thus, unless expressly stated otherwise, each feature disclosed is one example only of a generic series of equivalent or similar features.

The invention is not restricted to the details of the foregoing embodiment(s). The invention extends to any novel one, or any novel combination, of the features disclosed in this specification (including any accompanying claims, abstract and drawings), or to any novel one, or any novel combination, of the steps of any method or process so disclosed.

The invention claimed is:

1. A skin treatment apparatus comprising:
   a microwave source for generating microwave electromagnetic energy; and
   an applicator for mounting over a region of skin, the applicator comprising:
      an energy delivery structure for conveying the microwave electromagnetic energy; and
      a microwave feed structure coupled between the microwave source and the energy delivery structure for launching the microwave electromagnetic energy into the energy delivery structure,
   wherein the apparatus is controllable to deliver the microwave electromagnetic energy in a manner that induces a thermal profile in the region of skin, the thermal profile having a maximum temperature that occurs at a predetermined distance beneath a surface of the region of skin, and
   wherein the energy delivery structure comprises a waveguide having a waveguide body that defines a waveguide cavity having an interior electrically conductive surface dimensioned to support propagation of the microwave electromagnetic energy, wherein the waveguide cavity comprises a treatment aperture for locating over the region of skin, the treatment aperture being dimensioned to emit the microwave electromagnetic energy as an electromagnetic field,
   wherein the applicator comprises a deformable contact portion comprising a deformable rim on the waveguide body around the aperture, and
   wherein the deformable rim has a metallized inner surface that is electrically connected to the interior electrically conductive surface of the waveguide cavity.

2. The skin treatment apparatus according to claim 1, wherein the waveguide comprises a microwave shield on an interior wall adjacent the treatment aperture, the shield covering or occupying part or parts of the interior wall, and wherein the microwave shield is arranged to shape the emitted microwave electromagnetic energy as a uniform electromagnetic field across the treatment aperture.

3. The skin treatment apparatus according to claim 2, wherein the microwave shield is made from dielectric material or metamaterial arranged to create a quasi perfect magnetic conductor boundary condition at two opposing sides of the aperture.

4. The skin treatment apparatus according to claim 3, wherein the waveguide of the applicator is dimensioned to carry the microwave frequency electromagnetic energy in a fundamental mode, and wherein the electromagnetic field emitted by the waveguide is in a quasi-TEM mode.

5. The skin treatment apparatus according to claim 1, wherein the deformable rim is detachable from the waveguide body.

6. The skin treatment apparatus according to claim 1, comprising a loading unit mountable on the waveguide to load the waveguide.

7. The skin treatment apparatus according to claim 6, wherein the loading unit is arranged to shape the microwave electromagnetic energy emitted by the waveguide.

8. The skin treatment apparatus according to claim 7, wherein the loading unit is arranged to shape the microwave electromagnetic energy into a fractionated electromagnetic field.

9. The skin treatment apparatus according to claim 6, wherein the waveguide comprises a waveguide body that defines a waveguide cavity having an interior electrically conductive surface dimensioned to support propagation of the microwave electromagnetic energy, wherein the waveguide cavity comprises a treatment aperture for locating over the region of skin, and wherein the loading unit is arranged as a cover mountable in or over the treatment aperture.

10. The skin treatment apparatus according to claim 9, wherein the cover is made of an electrical insulator or a dielectric material.

11. The skin treatment apparatus according to claim 1, wherein the energy delivery structure comprises a flexible substrate having a microwave emitting structure fabricated thereon.

12. The skin treatment apparatus according to claim 11, wherein the microwave emitting structure is a slotted microstrip antenna.

13. The skin treatment apparatus according to claim 1, wherein the deformable contact portion is for abutting the region of skin.

14. The skin treatment apparatus according to claim 1, wherein the amount of power generated by the microwave source is controllable.

15. The skin treatment apparatus according to claim 14, wherein the microwave source includes a monitoring system configured to detect the power delivered to the waveguide, and wherein the power generated by the microwave source is controlled on the basis of the delivered power detected by the monitoring system.

16. The skin treatment apparatus according to claim 1, wherein the applicator comprises an imaging device arranged to capture an image of the region of skin during treatment.

17. The skin treatment apparatus according to claim 16, wherein the imaging device is arranged to detect infrared radiation.

18. The skin treatment apparatus according to claim 17, wherein the imaging device is arranged to generate an output indicative of temperature at the surface of the region of skin, and wherein the microwave source is controllable based on the output from the imaging device.

19. The skin treatment apparatus according to claim 1 comprising a cooling medium, wherein the cooling medium is arranged to induce a negative thermal gradient through the region of skin, and wherein the delivered microwave electromagnetic energy is arranged to induce a positive thermal gradient through the region of skin, and wherein the apparatus is arranged to balance the negative thermal gradient and positive thermal gradient to induce the thermal profile.

20. The skin treatment apparatus according to claim 1 including a cooling system configured to deliver a cooling medium through the waveguide to the aperture.

* * * * *